United States Patent [19]

Nomoto et al.

[11] Patent Number: 5,063,227
[45] Date of Patent: Nov. 5, 1991

[54] QUINAZOLINE-SUBSTITUTED PYRIDAZINONE DERIVATIVES HAVING CARDIOTONIC ACTIVITY

[75] Inventors: Yuji Nomoto; Haruki Takai; Tetsuji Ohno; Kazuhiro Kubo, all of Shizuoka, Japan

[73] Assignee: Kyowa Hakko Kogyo Co., Ltd., Tokyo, Japan

[21] Appl. No.: 462,914

[22] Filed: Jan. 11, 1990

Related U.S. Application Data

[63] Continuation of Ser. No. 297,440, Jan. 17, 1989, abandoned.

[30] Foreign Application Priority Data

Jan. 23, 1988 [JP] Japan ................. 63-13301

[51] Int. Cl.$^5$ ............... C07D 403/02; A61K 31/50
[52] U.S. Cl. ................. 514/252; 514/218; 514/235.8; 544/239; 540/575
[58] Field of Search ................. 544/238; 514/252

[56] References Cited

U.S. PATENT DOCUMENTS

| 4,053,600 | 10/1977 | Hardtmann | 514/252 |
| 4,672,116 | 6/1987 | Bandorco | 544/287 |
| 4,829,066 | 5/1989 | Spada et al. | 544/238 |
| 4,847,251 | 7/1989 | Mertens | 514/252 |
| 4,868,300 | 9/1989 | Kuhla | 544/238 |
| 4,923,869 | 5/1990 | Prücher | 544/238 |
| 4,946,842 | 7/1990 | Coates | 514/252 |
| 4,957,920 | 8/1990 | Mörsdorf et al. | 514/252 |
| 4,963,683 | 11/1990 | Mosdorf | 544/238 |

FOREIGN PATENT DOCUMENTS

| 0053479 | 3/1984 | Japan | 544/238 |
| 0139172 | 6/1988 | Japan | 514/239 |

OTHER PUBLICATIONS

Leistner et al., Zeitschrift fur Chemie, vol. 12, No. 8 (1972), p. 289.

Primary Examiner—Donald G. Daus
Attorney, Agent, or Firm—Fitzpatrick, Cella, Harper & Scinto

[57] ABSTRACT

Compounds of the formula

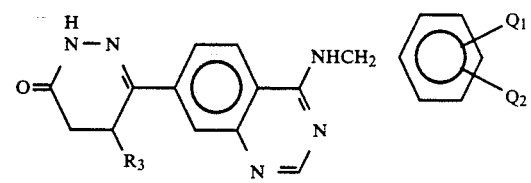

wherein $R_3$ is H or alkyl, $Q_1$ and $Q_2$ are independently hydrogen, alkyl, hydroxyl, alkoxyl, amino, mono or di alkylamino, nitro or halo or pharmaceutically acceptable salts are useful as cardiotonics.

3 Claims, No Drawings

QUINAZOLINE-SUBSTITUTED PYRIDAZINONE DERIVATIVES HAVING CARDIOTONIC ACTIVITY

This application is a continuation of application Ser. No. 07/297,440, filed Jan. 17, 1989, now abandoned.

BACKGROUND OF THE INVENTION

The present invention relates to novel pyridazinone derivatives having cardiotonic activity and to pharmaceutically acceptable acid addition salts thereof.

As the compounds having pyridazinone ring and which exhibit cardiotonic activity, there have been disclosed pimobendan of the following formula:

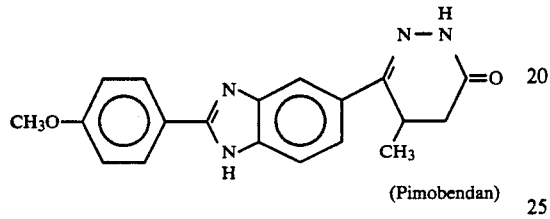

(Pimobendan)

[Japanese Published Unexamined Patent Application No. 33479/80 (U.S. Pat. No. 4,361,563)], LY195115 of the following formula:

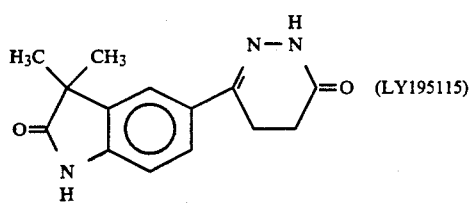

(LY195115)

[Japanese Published Unexamined Patent Application No. 22080/86 (EP 161918A)], CI-930 of the following formula:

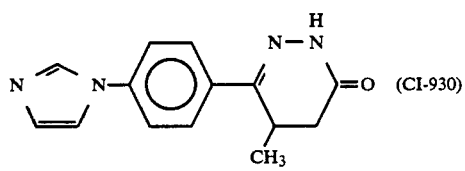

(CI-930)

[Japanese Published Unexamined Patent Application No. 74679/83 (EP 75436A)], etc. Further, as the compounds having pyridone ring and which exhibit cardiotonic activity, milrinone of the following formula:

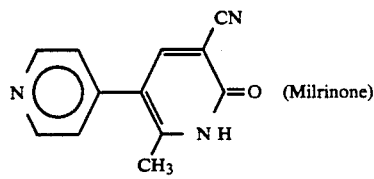

(Milrinone)

[Japanese Published Unexamined Patent Application No. 70868/82 (U.S. Pat. No. 4,297,360)], etc. have been disclosed.

Cardiotonics have been used for the treatment of chronic cardiac insufficiency. However, the known cardiotonics are still unsatisfactory in effectiveness and duration of effectiveness.

SUMMARY OF THE INVENTION

Novel pyridazinone derivatives which exhibit excellent cardiotonic activity are provided by the present invention.

The present invention relates to pyridazinone derivatives represented by the following formula (I):

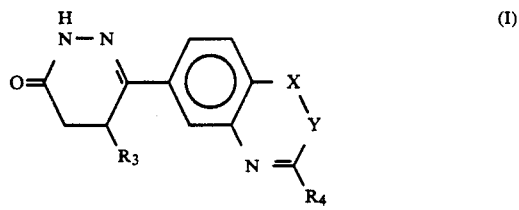

wherein
X—Y is —CH$_2$—NH—;

wherein $R_a$ is hydrogen; lower alkyl; —NR$_1$R$_2$ wherein R$_1$ and R$_2$ are independently hydrogen, optionally substituted lower alkyl, alicyclic alkyl, lower alkenyl, optionally substituted aralkyl, optionally substituted aryl, amino, lower alkoxycarbonylamino or

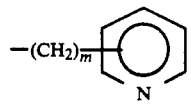

wherein m is 1 or 2, or R$_1$ and R$_2$ together represent an nitrogen-containing heterocyclic group; hydroxyl; lower alkoxyl; mercapto; lower alkylthio; or —SCH-(COOR$_5$)$_2$ wherein R$_5$ is lower alkyl;

wherein R$_b$ is an oxygen atom, a sulfur atom, C(COOR$_5$)$_2$ wherein R$_5$ has the same meaning as defined above, or NR$_{1a}$; and R$_{1a}$ and R$_{2a}$ are independently hydrogen, optionally substituted lower alkyl, alicyclic alkyl, lower alkenyl, optionally substituted aralkyl, optionally substituted aryl, amino, lower alkoxycarbonylamino, or

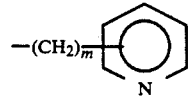

wherein m has the same meaning as defined above;

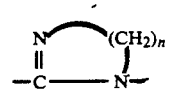

wherein n is 2 or 3; or

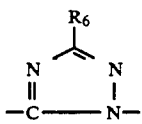

wherein $R_6$ is hydrogen or lower alkyl;
$R_3$ is hydrogen or lower alkyl; and
$R_4$ is hydrogen, optionally substituted lower alkyl, hydroxyl, lower alkoxyl, mercapto, lower alkylthio, or $-NR_1R_2$ wherein $R_1$ and $R_2$ have the same meanings as defined above;
and pharmaceutically acceptable acid addition salts thereof [the pyridazinone derivatives of formula (I) are hereinafter referred to as Compound (I); the same shall apply to the compounds of other formula numbers].

DETAILED DESCRIPTION OF THE INVENTION

In the definitions of the groups in formula (I), the alkyl moiety in the lower alkyl, lower alkoxycarbonylamino, lower alkoxyl and lower alkylthio groups is a straight-chain or branched alkyl group having 1 to 8 carbon atoms. Examples of such groups include methyl, ethyl, propyl, isopropyl, butyl, isobutyl, sec-butyl, tert-butyl, pentyl, isopentyl, neopentyl, sec-pentyl, tert-pentyl, hexyl, isohexyl, heptyl, octyl and isooctyl. The substituted alkyl group contains 1 to 3 substituents, which may be the same or different, such as hydroxyl, lower alkoxyl, carboxyl, lower alkoxycarbonyl, amino, mono- or di-alkyl-substituted amino, nitrogen-containing aliphatic heterocyclic group, nitro and halogen; the alkyl moiety in the lower alkoxyl, lower alkoxycarbonyl, mono- or di-alkyl-substituted amino groups is a straight-chain or branched alkyl group containing 1 to 4 carbon atoms such as methyl, ethyl, propyl, isopropyl, butyl, isobutyl, sec-butyl and tert-butyl, the nitrogen-containing aliphatic heterocyclic group includes pyrrolidinyl, piperidino, piperazinyl, N-methylpiperazinyl, morpholino, thiomorpholino, homopiperazinyl and N-methylhomopiperazinyl, and the halogen includes fluorine, chlorine, bromine and iodine.

The alicyclic alkyl group has 3 to 8 carbon atoms, and includes cyclopropyl, cyclopentyl, cyclohexyl and cyclooctyl.

The lower alkenyl represents an alkenyl group having 2 to 6 carbon atoms, and includes vinyl, allyl, propenyl, butenyl and hexenyl.

The aralkyl group has 7 to 15 carbon atoms, and includes benzyl, phenethyl and benzhydril. The aryl group has 6 to 10 carbon atoms, and includes phenyl and naphthyl. The aryl group and the aromatic ring moiety of the aralkyl group contain 1 to 2 substituents, which may be the same or different, such as hydroxyl, lower alkoxyl, amino, mono-or di-alkyl-substituted amino, nitro and halogen; and the lower alkoxyl, mono- or di-alkyl-substituted amino and halogen respectively represent the same as in the above definitions of the substituents in the substituted alkyl group.

The nitrogen-containing heterocyclic group formed by $R_1$ together with $R_2$ includes the same groups as the nitrogen-containing aliphatic heterocyclic group.

Some of Compounds (I) show tautomerism. For example, Compound (I) wherein $R_{2a}$ is hydrogen is represented by the following tautomers. All the tautomers of Compound (I) are included within the scope of the present invention.

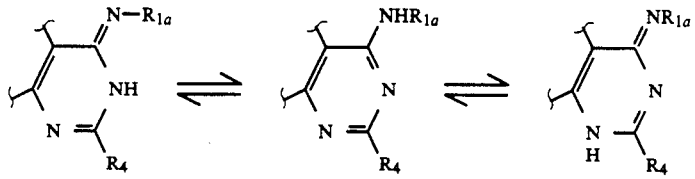

The pharmaceutically acceptable acid addition salts of Compound (I) include salts with various inorganic acids such as hydrochloride, hydrobromide, hydroiodide, nitrate, sulfate and phosphate, and salts with various organic acids such as formate, acetate, benzoate, maleate, fumarate, succinate, tartrate, citrate, oxalate, glyoxalate, aspartate, methanesulfonate and benzenesulfonate.

The processes for producing Compound (I) are described below.

Compound (I) can be produced from Compounds (IIa-c) which can be prepared by the following reaction steps:

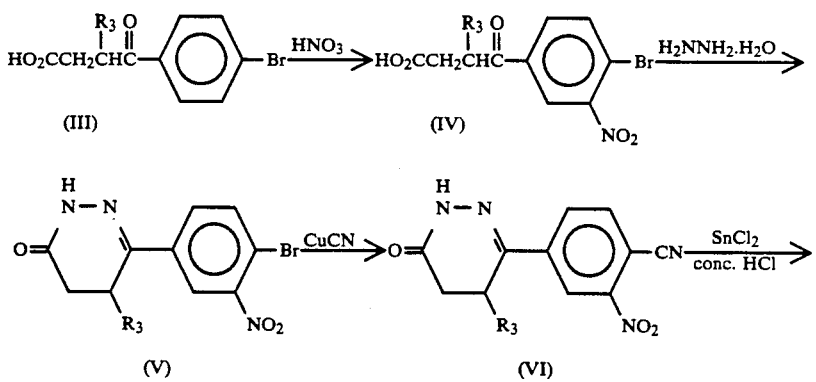

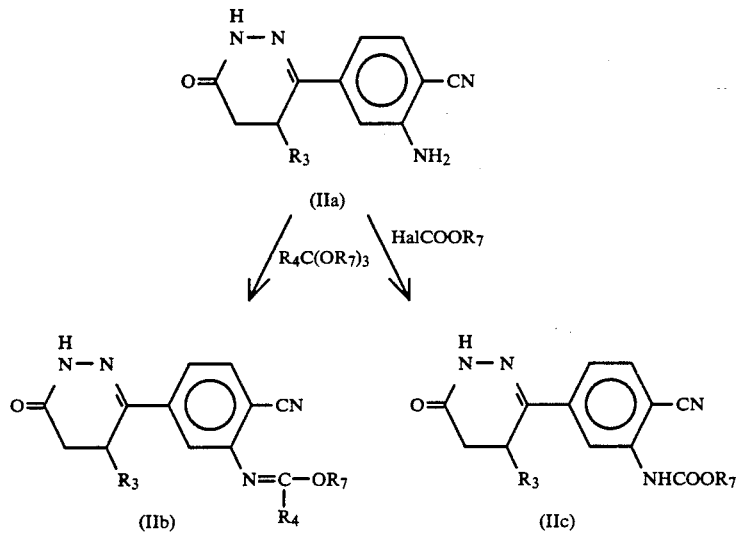

In the above formulae, $R_3$ and $R_4$ have the same meanings as defined above; $R_7$ represents alkyl or aryl; and Hal represents halogen. The alkyl in the definition of $R_7$ represents an alkyl group having 1 to 3 carbon atoms such as methyl, ethyl, propyl and isopropyl; the aryl represents phenyl, etc.; and halogen represented by Hal is chlorine, bromine, iodine, etc.

First, Compound (III) [J. Org. Chem., 38, 4044 (1973), etc.] is allowed to react with fuming nitric acid to obtain the nitro (IV). Compound (IV) is allowed to react with hydrazine to obtain the cyclized pyridazinone (V), which is then subjected to reaction with copper cyanide to obtain the cyano (VI). Compound (VI) is then reduced to obtain Compound (IIa).

Compound (IIb) can be obtained by allowing Compound (IIa) to react with an orthoester. Compound (IIc) can be obtained by allowing Compound (IIa) to react with a halogenated formic acid ester.

Process A

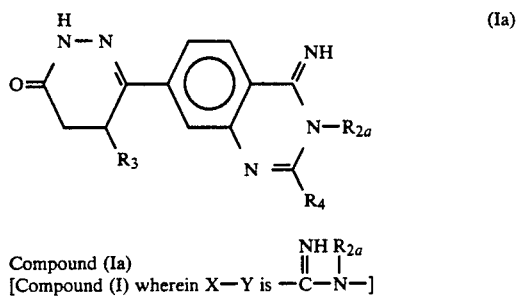

Compound (Ia)
[Compound (I) wherein X—Y is $-\overset{\underset{\parallel}{NHR_{2a}}}{C}-\overset{\underset{\parallel}{}}{N}-$]

In the formula, $R_{2a}$, $R_3$ and $R_4$ have the same meanings as defined above.

Compound (Ia) can be produced by subjecting Compound (IIb) to reaction with Compound (VIIa) of the following formula:

$$R_{2a}NH_2 \qquad (VIIa)$$

(in which $R_{2a}$ has the same meaning as defined above).

Compound (VIIa) is used preferably at least in an equivalent amount based on Compound (IIb), and may be used in large excess in the case where it serves also as a solvent.

It is also possible to use Compound (VIIa) in the form of an acid addition salt. The reaction is carried out preferably in the presence of a base at least in an equivalent amount based on Compound (VIIa). As the acid addition salt, those mentioned above as the acid addition salts of Compound (I) may be used. As the base, hydroxides of alkali metals such as sodium hydroxide and potassium hydroxide, alkoxides such as sodium methoxide and potassium ethoxide, amines such as triethylamine and pyridine, etc. may be used.

The reaction may be carried out without using any solvent, or in a solvent inert to the reaction. As the solvent, water, alcohols such as methanol and ethanol, aprotic polar solvents such as dimethylformamide and dimethylsulfoxide, halogenated hydrocarbons such as dichloromethane and chloroform, etc. may be used.

The reaction is carried out at a temperature between 0° C. and the boiling point of the solvent used and is completed in 10 minutes to 12 hours.

Process B

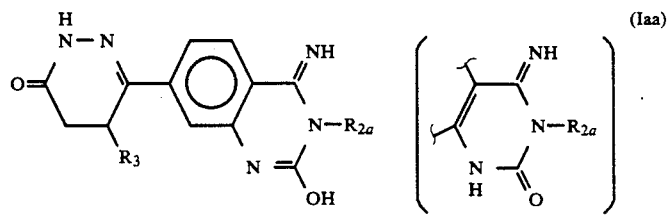

Compound (Iaa) [Compound (Ia) wherein $R_4$ is hydroxyl]

In the formula, $R_{2a}$ and $R_3$ have the same meanings as defined above.

Compound (Iaa) can be obtained in a similar manner as in Process A using Compound (VIIa) and Compound (IIc) in place of Compound (IIb).

Process C

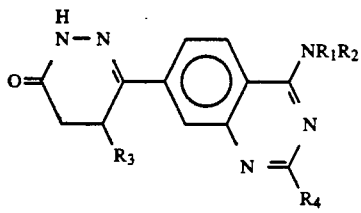

Compound (Ib)
[Compound (I) wherein X—Y is $-\overset{NR_1R_2}{\underset{|}{C}}=N-$]

In the formula, $R_1$, $R_2$, $R_3$ and $R_4$ have the same meanings as defined above.

Compound (Ib) can be obtained by subjecting Compound (VIII) of the following formula:

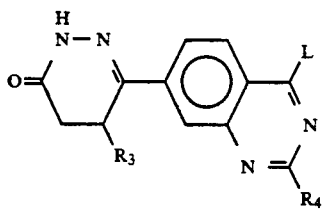

(wherein $R_3$ and $R_4$ have the same meanings as defined above; and L represents a leaving group) to reaction with Compound (VIIb) of the following formula:

$R_1R_2NH$ (VIIb)

(wherein $R_1$ and $R_2$ have the same meanings as defined above).

The leaving group represented by L includes mercapto groups, halogen atoms such as chlorine and bromine, alkoxyl groups such as methoxy and ethoxy, alkylthio groups such as methylthio and ethylthio, arylthio groups such as phenylthio, alkylsulfinyl groups such as methylsulfinyl and ethylsulfinyl, arylsulfinyl groups such as phenylsulfinyl, lower alkylsulfonyl groups such as methylsulfonyl, trifluoromethylsulfonyl and ethylsulfonyl, arylsulfonyl groups such as phenylsulfonyl and p-toluenesulfonyl, etc.

Compound (VIIb) is used in an amount ranging from an equivalent amount to a large excess based on Compound (VIII). If desired, tertiary amines such as triethylamine may be used in order to accelerate the reaction.

The reaction may be carried out without using any solvent or in a suitable solvent. As the solvent, water, alcohols such as methanol and ethanol, aprotic polar solvents such as dimethylformamide and dimethylsulfoxide, etc. can be preferably used.

The reaction is carried out at a temperature between room temperature and the boiling point of the solvent used, and is completed in 10 minutes to 24 hours.

The starting material, Compound (VIII), can be prepared by Process H or J shown below, or by subjecting the compounds obtained by Process H or J to oxidation, halogenation, etc. in a conventional manner.

Process D

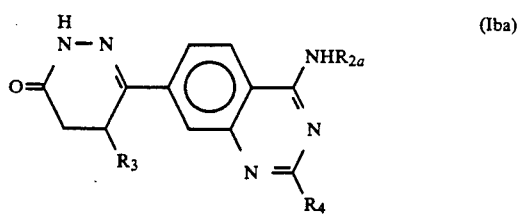

Compound (Iba)
[Compound (Ib) wherein $-NR_1R_2$ is $-NHR_{2a}$]

In the formula, $R_{2a}$, $R_3$ and $R_4$ have the same meanings as defined above.

Compound (Iba) can be obtained by treating Compound (Ia) which is obtained by Process A with a base.

As the reaction solvent, water, alcohols such as methanol and ethanol, aprotic polar solvents such as dimethylformamide and dimethylsulfoxide, etc. can be preferably used.

As the base, those mentioned in Process A may be used.

The reaction is carried out at a temperature between room temperature and the boiling point of the solvent used, and is completed in 10 minutes to 24 hours.

Process E

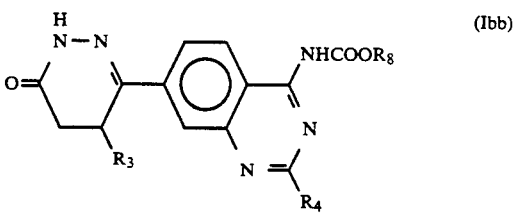

Compound (Ibb) [Compound (Ib) wherein $-NR_1R_2$ is lower alkoxycarbonylamino]

In the formula, $R_3$ and $R_4$ have the same meanings as defined above; and $R_8$ represents lower alkyl.

The lower alkyl group represented by $R_8$ has the same meaning as in the definition of the lower alkyl group in formula (I).

Compound (Ibb) can be obtained by allowing Compound (Ib) wherein X-Y is

$-\overset{NH_2}{\underset{|}{C}}=N-$, which can be prepared by Process C, to react with Compound (IX) of the following formula:

HalCOOR$_8$ (IX)

(wherein $R_8$ and Hal have the same meanings as defined above) in the presence of a base.

As the base, those mentioned in Process A may be used. As the solvent, dimethylformamide, halogenated hydrocarbons such as dichloromethane and chloroform, etc. can be used. Alternatively, it is possible to use a base such as pyridine and triethylamine also as the solvent. The reaction is carried out at 0° to 100° C. and is completed in 10 minutes to 12 hours.

Process F

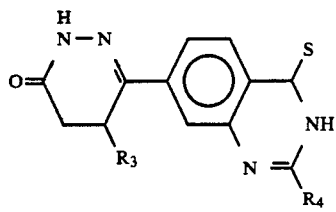

Compound (Ic) [Compound (I) wherein X—Y is

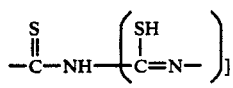

]

In the formula, $R_3$ and $R_4$ have the same meanings as defined above.

Compound (Ic) can be obtained by subjecting Compound (IIb) to reaction with hydrogen sulfide in a basic solvent such as pyridine and triethylamine or in a mixture of such a basic solvent and another solvent. The reaction is carried out by introducing hydrogen sulfide gas into the solution of Compound (IIb) at a temperature between 0° C. and the boiling point of the solvent used, and is completed in 10 minutes to 3 hours.

Process G

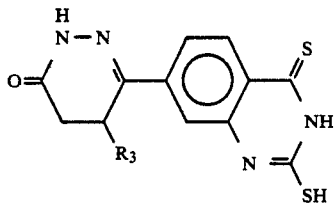

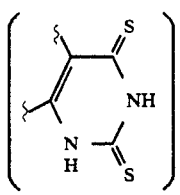

Compound (Ica) [Compound (Ic) wherein $R_4$ is mercapto]

In the formula, $R_3$ has the same meaning as defined above.

Compound (Ica) can be obtained in a similar manner as in Process F using Compound (IIa) and carbon disulfide in place of Compound (IIb) and hydrogen sulfide, respectively.

Process H

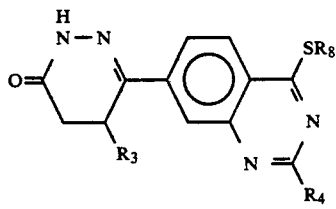

Compound (Id) [Compound (I) wherein X—Y is

]

In the formula, $R_3$, $R_4$ and $R_8$ have the same meanings as defined above.

Compound (Id) can be obtained by allowing Compound (Ic) which can be prepared by Process F to react with an alkylating agent such as halogenated alkyl and diazoalkane in the presence of a base.

As the base, sodium hydroxide, potassium carbonate, diazabicycloundecene (DBU), triethylamine, pyridine, dimethylaminopyridine, sodium hydride, etc. may be used.

The reaction is carried out in a solvent inert to the reaction. The inert solvent includes water, alcohols such as methanol and ethanol, aprotic polar solvents such as dimethylformamide and dimethylsulfoxide, halogenated hydrocarbons such as dichloromethane and chloroform, etc.

The reaction is carried out at a temperature between 0° C. and the boiling point of the solvent used, and is completed in 10 minutes to 12 hours.

Process I

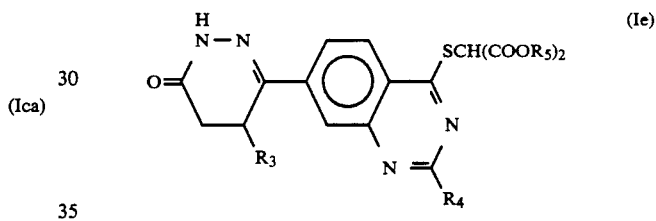

Compound (Ie) [Compound (I) wherein X—Y is
$$\begin{matrix} SCH(COOR_5)_2 \\ | \\ -C=N- \end{matrix}$$
]

In the formula, $R_3$, $R_4$ and $R_5$ have the same meanings as defined above.

Compound (Ie) can be obtained in a similar manner as in Process H using Compound (X) of the following formula:

$$HalCH(COOR_5)_2 \qquad (X)$$

(wherein $R_5$ and Hal have the same meanings as defined above) as the alkylating agent.

Process J

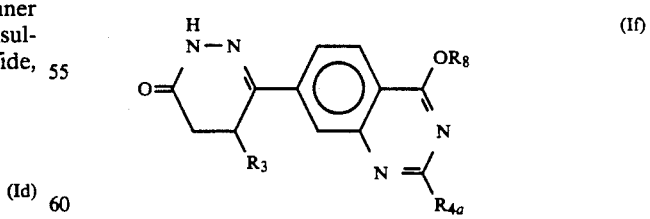

Compound (If) [Compound (I) wherein X—Y is
$$\begin{matrix} OR_8 \\ | \\ -C=N- \end{matrix}$$
]

In the formula, $R_3$ and $R_8$ have the same meanings as defined above; and $R_{4a}$ represents the same lower alkyl groups as those in the definition of $R_4$.

Compound (If) can be obtained in the following manner.

First, Compound (IIa) is allowed to react with a suitable acylating agent to obtain Compound (IId).

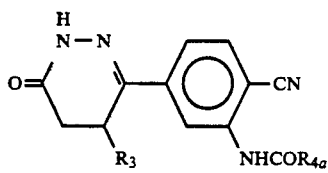
(IId)

(In the formula, $R_3$ and $R_{4a}$ have the same meanings as defined above).

The suitable acylating agent includes acid anhydrides, acid halides, etc. of the corresponding carboxylic acids.

Compound (IId) is then allowed to react with an alcohol (XI) of the following formula:

$R_8OH$ (XI)

(wherein $R_8$ has the same meaning as defined above) in the presence of a base to give Compound (If).

The above reactions are carried out under the same conditions as in Process H using the same base and reaction solvents.

Process K

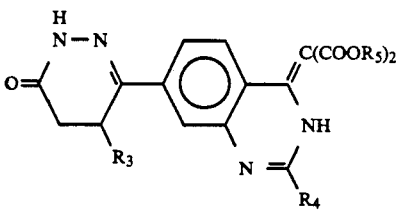
(Ig)

Compound (Ig) [Compound (I) wherein X—Y is
$\underset{\underset{-C-NH-}{\|}}{C(COOR_5)_2}$ ]

In the formula, $R_3$, $R_4$ and $R_5$ have the same meanings as defined above.

Compound (Ig) can be obtained by treating Compound (Ie) which can be obtained by Process I with triphenylphosphine in the presence of a base.

The reaction is carried out under the same conditions as in Process H using the same base and reaction solvent.

Process L

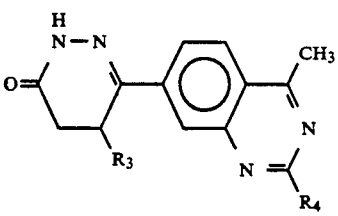
(Ih)

Compound (Ih) [Compound (I) wherein X—Y is
$\underset{-C=N-}{\overset{CH_3}{|}}$ ]

In the formula, $R_3$ and $R_4$ have the same meanings as defined above.

Compound (Ih) can be obtained by subjecting Compound (Ig) which can be obtained by Process K to saponification under alkaline conditions.

The reaction is carried out in an aqueous solution of an alkali such as sodium hydroxide and potassium hydroxide or in a solvent mixture of such solution and an alcohol (e.g., methanol and ethanol) at a temperature between room temperature and the boiling point of the solvent used, and is completed in 10 minutes to 12 hours.

Process M

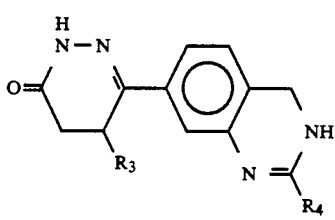
(Ii)

Compound (Ii) [Compound (I) wherein X—Y is
—CH$_2$—NH—]

In the formula, $R_3$ and $R_4$ have the same meanings as defined above.

Compound (Ii) can be obtained by subjecting Compound (Id) which can be obtained by Process H to reduction (desulfurization).

As the reducing agent, Raney nickel is preferably used. The reaction is carried out in a solvent such as water, alcohols (e.g., methanol and ethanol) and dimethylformamide at a temperature between room temperature and the boiling point of the solvent used, and is completed in 30 minutes to 12 hours.

Process N

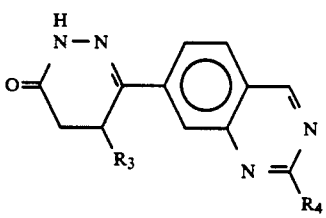
(Ij)

Compound (Ij) [Compound (I) wherein X—Y is
—CH=N—]

In the formula, $R_3$ and $R_4$ have the same meanings as defined above.

Compound (Ij) can be obtained by oxidizing Compound (Ii) which can be obtained by Process M.

As the oxidizing agent, manganese dioxide, chromic acid, hydrogen peroxide, etc. are suitable. The reaction is carried out at 0° C. to 50° C. and completed in 10 minutes to 12 hours.

Process O

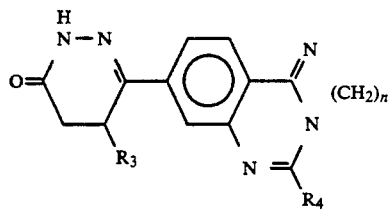

Compound (Ik) [Compound (I) wherein X—Y is $$\underset{-C-N-}{\overset{N\frown(CH_2)_n}{\overset{\|}{\phantom{C}}}}\hspace{0.3cm}]$$

In the formula, R$_3$, R$_4$ and n have the same meanings as defined above.

Compound (Ik) can be obtained from Compound (IIb) and Compound (VIIc) of the following formula:

$$H_2N(CH_2)_nNH_2 \hspace{3cm} (VIIc)$$

(wherein n has the same meaning as defined above) or an acid addition salt thereof in a similar manner as in Process A.

Compound (Ik) wherein R$_4$ is hydroxyl can also be obtained by using Compound (IIc) in place of Compound (IIb).

Process P

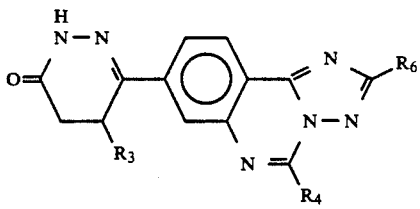

Compound (Il) [Compound (I) wherein X—Y is $$\underset{-C\rule{0.6cm}{0.4pt}N-]}{\overset{R_6}{\overset{\diagup\hspace{-0.1cm}\diagdown}{\underset{\|\hspace{0.5cm}|}{N\hspace{0.5cm}N}}}}$$

In the formula, R$_3$, R$_4$ and R$_6$ have the same meanings as defined above.

Compound (Il) can be obtained by allowing Compound (Ia) wherein X-Y is $$\underset{C-N-}{\overset{NH\ NH_2}{\overset{\|\ \ |}{\phantom{C}}}}$$

prepared by Process A to react with Carboxylic Acid (XII) of the following formula:

$$R_6COOH \hspace{3cm} (XII)$$

(wherein R$_6$ has the same meaning as defined above) or a reactive derivative thereof (e.g., esters, orthoesters and acid halides).

In the above reaction, Compound (XII) is used in a large excess so as to allow it to function also as a reaction solvent. The reaction is carried out at a temperature between room temperature and the boiling point of the solvent, and is completed in 30 minutes to 12 hours.

Process Q

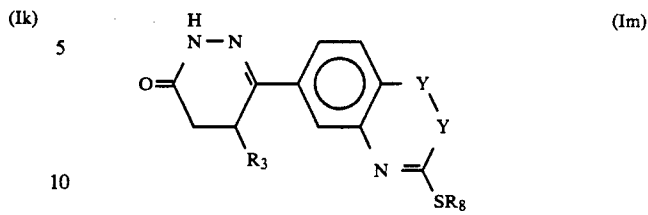

Compound (Im) [Compound (I) wherein R$_4$ is alkylthio]

In the formula, X-Y, R$_3$ and R$_8$ have the same meanings as defined above.

Compound (Im) can be obtained in a similar manner as in Process H from Compound (Ica) wherein R$_4$ is a mercapto group which can be obtained by Process G.

Process R

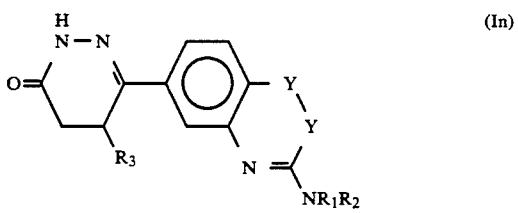

Compound (In) [Compound (I) wherein R$_4$ is —NR$_1$R$_2$]

In the formula, X-Y, R$_1$, R$_2$ and R$_3$ have the same meanings as defined above.

Compound (In) can be obtained by oxidizing the alkylthio group of Compound (Im) which is obtainable by Process Q with a suitable oxidizing agent and then allowing the oxidized product to react with Amine (VIIb).

The suitable oxidizing agent includes potassium permanganate, hydrogen peroxide, m-chloroperbenzoic acid, etc. The reaction of the oxidized product with Amine (VIIb) can be carried out in a similar manner as in Process C.

Process for producing Compound (I), as well as processes for producing Compounds (IIa-c) which are starting compounds, are not limited to those described above.

For example, the ring closure utilizing hydrazine can be carried out as the last step in each process. It is possible to first prepare Precursors (XIIIa-c) from Compound (IV) in accordance with the processes described above.

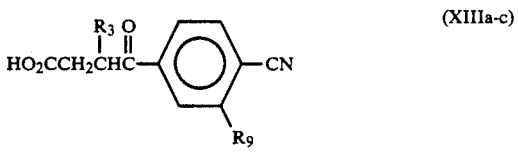

In the formula, R$_9$ is —NH$_2$(XIIIa), —N=C-R$_4$—OR$_7$ (XIIIb) or —NHCOOR$_7$(XIIIc); and R$_3$, R$_4$ and R$_7$ have the same meanings as defined above.

The thus obtained Compound (XIIIa-c) is then subjected to reaction for forming a quinazoline ring in a similar manner as in Process A to R described above, and then to reaction with hydrazine for forming a pyridazinone ring to give Compound (I).

The intermediates and the desired products in the processes described above can be isolated and purified by the purification methods conventionally employed in the organic synthetic chemistry, for example, filtration, extraction, washing, drying, concentration, recrystallization and various kinds of chromatography. The intermediates can be employed in the next step without substantial purification.

In the case where a salt of Compound (I) is desired and it is produced in the form of the desired salt, it can be subjected to purification as such. In the case where Compound (I) is produced in the free state and its salt is desired, it can be converted into its salt in a conventional manner.

Compound (I) and pharmaceutically acceptable salts thereof sometimes exist in the form of an addition product with water or with a solvent. Such addition products are also included within the scope of the present invention.

Moreover, in addition to the tautomers described above, all the possible stereoisomers of Compound (I) and their mixtures are also included within the scope of the present invention.

Specific examples of Compound (I) obtained by the above-described processes and the physical properties thereof are shown in Tables 1-1 to 1-6.

TABLE 1-1

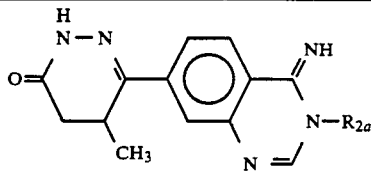

| Compound No. (Example No.) | R$_{2a}$ | Melting point (°C.) | IR KBr (cm$^{-1}$) | NMR (δ) ppm (Solvent) |
|---|---|---|---|---|
| 1 (1) | —CH$_3$ | 253 to 255 | 1680 1630 1590 | 11.1, 8.2, 8.0, 7.8, 7.7, 3.5, 3.4, 2.7, 2.3, 1.1 (CDCl$_3$) |
| 2 (2) | —CH$_2$CH$_3$ | 238 to 244 | 1680 1620 1600 | 11.1, 8.2, 8.1, 7.8, 4.0, 3.5, 2.7, 2.3, 1.2, 1.1 (DMSO-d$_6$) |
| 3 | —(CH$_2$)$_2$CH$_3$ | 239 | 1680 | 11.1, 8.2, 8.0, |

TABLE 1-1-continued

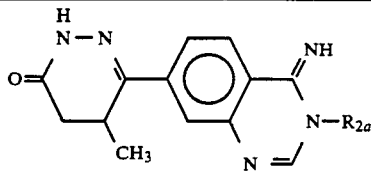

| Compound No. (Example No.) | R$_{2a}$ | Melting point (°C.) | IR KBr (cm$^{-1}$) | NMR (δ) ppm (Solvent) |
|---|---|---|---|---|
| (3) | | to 240 | 1620 1600 | 7.8, 3.9, 3.5, 2.7, 2.3, 1.7, 1.1, 0.9 (DMSO-d$_6$) |
| 4 (4) | —CH(CH$_3$)$_2$ | 205 | 1690 1620 1600 | 11.1, 8.7, 8.2, 8.1, 7.8, 5.2, 3.5, 2.7, 2.2, 1.4, 1.1 (DMSO-d$_6$) |
| 5 (5) | —(CH$_2$)$_3$CH$_3$ | 198 to 200 | 1700 1630 1620 1600 | 11.1, 8.2, 8.0, 7.8, 7.7, 4.0, 3.5, 2.7, 2.3, 1.7, 1.3, 1.1, 0.9 (CDCl$_3$) |
| 6 (6) |  | 232 (decomp.) | 1700 1640 1620 | 11.1, 8.2, 8.0, 7.8, 4.5, 3.5, 3.0, 2.8, 2.3, 1.1, 0.9 (DMSO-d$_6$) |
| 7 (7) | 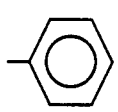 | 216 | 1700 1630 1600 | 11.1, 8.2, 7.8, 7.3, 5.2, 3.5, 2.8, 2.3, 1.1 (DMSO-d$_6$) |
| 8 (8) | ![phenyl] | 274 to 275 (decomp.) | 1680 1640 1600 | 11.2, 8.3, 8.0, 7.8, 7.6, 3.5, 2.8, 2.3, 1.1 (DMSO-d$_6$) |
| 9 (9) | —C$_6$H$_4$—OCH$_3$ | 268 | 1690 1630 1610 | 11.1, 8.2, 7.8, 7.4, 7.1, 3.8, 3.5, 2.8, 2.3, 1.1 (DMSO-d$_6$) |
| 10 (10) | —NH$_2$ | 193 | 1680 1640 1630 | 11.1, 8.3, 8.0, 7.8, 5.6, 3.5, 2.8, 2.3, 1.1 (DMSO-d$_6$) |

TABLE 1-2

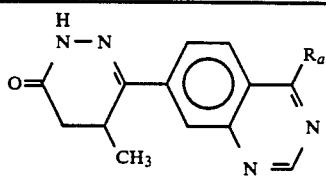

| Compound No. (Example No.) | R$_a$ | Melting Point (°C.) | IR KBr (cm$^{-1}$) | NMR (δ) ppm (Solvent) |
|---|---|---|---|---|
| 11 (11) | —NH$_2$ | >300 | 1700 1660 1560 | 11.1, 8.4, 8.2, 7.9, 7.8, 3.6, 2.8, 2.3, 1.1 (CDCl$_3$) |
| 11' (12) | Monohydrochloride monohydrate of | 256 to | — | — |

TABLE 1-2-continued

[Structure: pyridazinone with N-NH, C=O, CH3 substituent, connected to phenyl ring with Ra group and N=N (diazo) substituent]

| Compound No. (Example No.) | Ra | Melting Point (°C.) | IR KBr (cm$^{-1}$) | NMR (δ) ppm (Solvent) |
|---|---|---|---|---|
| | Compound 11 | 260 | | |
| 12 (13) | —NHCH$_3$ | 296 to 300 | 1680 1620 1530 | 11.1, 8.5, 8.4, 8.2, 8.0, 3.6, 3.0, 2.8, 2.3, 1.1 (CDCl$_3$) |
| 13 (20) | —N(CH$_3$)$_2$ | 235 to 237 | 1700 1570 1530 | 9.1, 8.6, 8.1, 8.0, 3.5, 3.4, 2.6, 1.1 (CDCl$_3$) |
| 14 (14) | —NHCH$_2$CH$_3$ | 261 to 266 | 1680 1620 1600 | 11.3, 10.6, 8.9, 8.7, 8.2, 8.1, 3.7, 3.5, 2.8, 2.3, 1.3, 1.1 (DMSO-d$_6$) |
| 15 (15) | —NH(CH$_2$)$_2$CH$_3$ | 263 to 269 | 1670 1620 1570 | 11.1, 8.5, 8.3, 7.9, 3.5, 2.8, 2.3, 1.7, 1.1, 0.9 (DMSO-d$_6$) |
| 16 (16) | —NHCH(CH$_3$)$_2$ | 259 to 261 | 1660 1620 1570 | 11.2, 8.6, 8.5, 8.4, 8.0, 4.5, 3.5, 2.8, 2.3, 1.2, 1.1 (DMSO-d$_6$) |
| 17 (21) | —NH(CH$_2$)$_3$CH$_3$ | 225 to 231 | 1670 1620 1580 | 11.1, 8.5, 8.2, 8.0, 3.5, 2.8, 2.2, 1.6, 1.4, 1.1, 0.9 (DMSO-d$_6$) |
| 18 (22) | —NHCH$_2$CH(CH$_3$)$_2$ | 285 to 286 | 1660 1620 1580 | 11.1, 8.4, 8.3, 7.9, 3.5, 3.4, 2.8, 2.3, 2.0, 1.1, 0.9 (DMSO-d$_6$) |
| 19 (23) | —NHCHCH$_2$CH$_3$<br>\|<br>CH$_3$ | >300 | 1680 1620 1580 | 11.1, 8.4, 8.3, 7.9, 4.4, 3.5, 2.8, 2.3, 1.6, 1.2, 1.1, 0.9 (DMSO-d$_6$) |
| 20 (24) | —NH(CH$_2$)$_4$CH$_3$ | 254 to 255 | 1670 1620 1580 | 11.1, 8.4, 8.2, 7.9, 3.5, 2.8, 2.3, 1.8-1.2, 1.1, 0.9, (DMSO-d$_6$) |
| 21 (25) | —NH(CH$_2$)$_2$CH(CH$_3$)$_2$ | 292 to 293 | 1670 1620 1570 | 11.1, 8.4, 8.2, 7.9, 3.5, 2.8, 2.3, 1.6, 1.1, 0.9 (DMSO-d$_6$) |
| 22 (26) | —NH(CH$_2$)$_5$CH$_3$ | 254 to 255 | 1660 1620 1570 | 11.1, 8.4, 8.2, 7.9, 3.5, 2.8, 2.3, 1.8-1.2, 1.1, 0.9 (DMSO-d$_6$) |
| 23 (27) | —NH(CH$_2$)$_6$CH$_3$ | 234 to 238 | 1670 1620 1580 | 11.1, 8.4, 8.2, 7.9, 3.5, 2.8, 2.3, 1.6, 1.3, 1.1, 0.9 (DMSO-d$_6$) |
| 24 (28) | —NH(CH$_2$)$_7$CH$_3$ | 224 to 225 | 1680 1620 1580 | 11.1, 8.4, 8.2, 7.9, 3.5, 2.8, 2.2, 1.8-1.2, 1.1, 0.9 (DMSO-d$_6$) |
| 25 (29) | —NHCH$_2$CH$_2$OH | 234 to 236 | 1680 1620 1580 | 11.1, 8.4, 8.3, 7.9, 4.8, 3.6, 2.8, 2.2, 1.1 (DMSO-d$_6$) |

TABLE 1-2-continued

[Structure: O=C-CH(CH3)-CH2-C(=N-NH-H)-phenyl-C(Ra)=N-N= (with fused ring)]

| Compound No. (Example No.) | Ra | Melting Point (°C.) | IR KBr (cm⁻¹) | NMR (δ) ppm (Solvent) |
|---|---|---|---|---|
| 26 (30) | —NHCH$_2$CH$_2$N(CH$_3$)$_2$ | 243 to 245 | 1670 1620 1580 | 11.1, 9.3, 8.7, 8.0, 7.8, 6.8, 3.7, 3.5, 2.7, 1.3 (DMSO-d$_6$) |
| 27 (31) | —NH(CH$_2$)$_3$N(morpholine) | 231 to 233 | 1680 1600 1580 | 11.2, 8.4, 8.2, 7.9, 3.6, 2.8, 2.4, 2.3, 1.8, 1.1 (DMSO-d$_6$) |
| 28 (17) | —NH-cyclopropyl | 286 to 287 (decomp.) | 1680 1620 1570 | 11.2, 8.6, 8.3, 8.0, 4.5, 3.1, 2.8, 2.3, 1.1, 0.8, 0.7 (DMSO-d$_6$) |
| 29 (32) | —NH-cyclopentyl | 262 (decomp.) | 1680 1620 1580 | 11.2, 8.4, 8.3, 7.9, 4.6, 3.5, 2.8, 2.3, 1.7, 1.1 (DMSO-d$_6$) |
| 30 (33) | —NH-cyclohexyl | 288 to 291 | 1670 1620 1570 | 11.2, 8.4, 8.3, 7.9, 4.2, 3.5, 2.8, 2.3, 2.1–1.2, 1.1 (DMSO-d$_6$) |
| 31 (34) | —NH-cyclooctyl | 289 to 290 | 1670 1620 1580 | 11.1, 8.4, 8.3, 7.9, 4.4, 3.5, 2.8, 2.3, 1.9–1.5, 1.1 (DMSO-d$_6$) |
| 32 (35) | —NHCH$_2$CH=CH$_2$ | 252 to 255 | 1670 1620 1570 | 11.1, 8.5, 8.3, 8.0, 6.0, 5.3, 5.1, 4.2, 2.8, 2.3, 1.1 (DMSO-d$_6$) |
| 33 (36) | —NHCH$_2$-phenyl | 248 | 1680 1620 1580 | 11.1, 8.8, 8.4, 8.3, 8.0, 7.3, 4.8, 3.5, 2.8, 2.2, 1.1 (DMSO-d$_6$) |
| 34 (37) | —NHCH$_2$-(2-CH$_3$-phenyl) | 287 (decomp.) | 1680 1620 1580 | 11.0, 8.7, 8.4, 8.0, 7.2, 4.7, 2.8, 2.3, 2.2, 1.1 (DMSO-d$_6$) |
| 35 (38) | —NHCH$_2$-(4-CH$_3$-phenyl) | 268 to 271 | 1660 1600 1560 | 11.1, 8.8, 8.5, 8.3, 8.0, 7.2, 4.8, 3.6, 2.8, 2.3, 2.2, 1.1 (DMSO-d$_6$) |
| 36 (39) | —NHCH$_2$-(2-OCH$_3$-phenyl) | >300 | 1670 1600 | 11.1, 8.6, 8.3, 8.0, 7.2, 6.9, 4.7, 3.8, 2.8, 2.3, 1.1 (DMSO-d$_6$) |

TABLE 1-2-continued

[Structure: pyridazinone with NH-N=, C=O, CH3 substituent, connected to phenyl ring bearing Ra and a CH=N-N group]

| Compound No. (Example No.) | Ra | Melting Point (°C.) | IR KBr (cm⁻¹) | NMR (δ) ppm (Solvent) |
|---|---|---|---|---|
| 37 (40) | —NHCH₂—⟨phenyl-3-OCH₃⟩ | 296 (decomp.) | 1670, 1620, 1580 | 11.0, 8.8, 8.4, 8.3, 7.2, 6.9, 4.7, 3.7, 2.8, 2.3, 1.1 (DMSO-d₆) |
| 38 (41) | —NHCH₂—⟨phenyl-4-OCH₃⟩ | 256 to 257 | 1690, 1620, 1570 | 11.1, 8.8, 8.4, 8.3, 7.9, 7.3, 6.9, 4.7, 3.7, 2.8, 2.3, 1.1 (DMSO-d₆) |
| 39 (42) | —NHCH₂—⟨phenyl-4-F⟩ | 264 | 1680, 1620, 1580 | 11.1, 8.8, 8.4, 8.2, 8.0, 7.4–7.1, 4.8, 3.5, 2.8, 2.3, 1.1 (DMSO-d₆) |
| 40 (43) | —NHCH₂—⟨phenyl-2-Cl⟩ | 219 to 224 | 1680, 1580 | 11.1, 8.8, 8.4, 8.3, 8.0, 7.4, 7.3, 4.8, 3.5, 2.8, 2.3, 1.1 (DMSO-d₆) |
| 41 (44) | —NHCH₂—⟨phenyl-3-Cl⟩ | 237 to 242 | 1680, 1580 | 11.0, 8.8, 8.4, 8.3, 8.0, 7.4, 7.3, 4.8, 3.5, 2.8, 2.3, 1.1 (DMSO-d₆) |
| 42 (45) | —NHCH₂—⟨phenyl-4-Cl⟩ | 276 to 278 | 1680, 1600, 1560 | 11.1, 8.8, 8.4, 8.3, 8.0, 7.3, 4.8, 3.5, 2.8, 2.3, 1.1 (DMSO-d₆) |
| 43 (46) | —NHCH₂CH₂—⟨phenyl⟩ | 264 to 265 | 1670, 1620, 1580 | 11.2, 8.5, 8.4, 8.2, 8.0, 7.3, 3.8, 3.5, 3.0, 2.8, 2.3, 1.2 (DMSO-d₆) |
| 44 (47) | —NHCH₂CH₂—⟨phenyl-3,4-(OCH₃)₂⟩ | >300 | 1680, 1600, 1580 | 11.1, 8.5, 8.2, 7.9, 6.8, 3.7, 2.9, 2.8, 2.3, 1.1 (DMSO-d₆) |
| 45 (48) | —NH—⟨phenyl⟩ | 286 to 289 (decomp.) | 1670, 1620, 1560 | 11.2, 9.9, 8.6, 8.1, 7.9, 7.4, 7.1, 3.5, 2.8, 2.3, 1.1 (DMSO-d₆) |
| 46 (49) | —NH—⟨phenyl-3-Cl⟩ | 293 to 294 | 1690, 1620, 1600 | 11.1, 8.6, 8.0, 7.8, 7.5–7.1, 3.5, 2.8, 2.3, 1.1 (DMSO-d₆) |

TABLE 1-2-continued

[Structure: pyridazinone-methyl-phenyl-C(=N-N=)-Ra core]

| Compound No. (Example No.) | $R_a$ | Melting Point (°C.) | IR KBr (cm$^{-1}$) | NMR (δ) ppm (Solvent) |
|---|---|---|---|---|
| 47 (50) | —NH—C₆H₄—Cl | >300 | 1670, 1620, 1560 | 11.1, 8.6, 8.0, 7.9, 7.4, 3.5, 2.8, 2.3, 1.1 (DMSO-d$_6$) |
| 48 (51) | —NHCH₂-(3-pyridyl) | 264 to 266 | 1680, 1620, 1570 | 11.1, 8.9–7.2, 4.8, 3.5, 2.8, 2.3, 1.1 (DMSO-d$_6$) |
| 49 (52) | —NHCH₂-(4-pyridyl) | 284 to 285 | 1680, 1620, 1580 | 11.1, 8.9, 8.4, 8.2, 8.0, 7.3, 4.8, 3.5, 2.8, 2.3, 1.1 (DMSO-d$_6$) |
| 50 (53) | —NHCH₂CH₂-(2-pyridyl) | 245 to 247 | 1670, 1620, 1580 | 11.2, 8.4, 8.2, 7.9, 7.6, 7.2, 3.9, 3.5, 3.1, 2.8, 2.3, 1.1 (DMSO-d$_6$) |
| 51 (54) | —N(piperazinyl)NH.2HCl | 209 to 211 | 1700, 1680, 1620, 1600 | 11.1, 9.9, 8.9, 8.4–8.0, 4.4, 3.4, 2.8, 2.2, 1.2 (DMSO-d$_6$) |
| 52 (55) | —N(piperidinyl) | 268 to 270 | 1700, 1620, 1560 | 11.1, 8.6, 8.0, 3.7, 3.5, 2.8, 2.3, 1.7, 1.1 (DMSO-d$_6$) |
| 53 (56) | —NHCO₂C₂H₅ | 261 to 265 | 1690, 1620, 1600 | 11.2, 10.7, 9.0, 8.4, 8.2, 4.2, 3.5, 2.8, 2.3, 1.3, 1.1 (DMSO-d$_6$) |
| 54 (72) | —H | 224 to 225 | 1680, 1620, 1560 | 11.2, 9.6, 9.3, 8.2, 3.6, 2.7, 2.3, 1.1 (DMSO-d$_6$) |
| 55 (59) | —CH₃ | 218 to 221 | 1690, 1620, 1560 | 11.1, 9.1, 8.2, 3.5, 2.9, 2.8, 2.3, 1.1 (DMSO-d$_6$) |
| 56 (18) | —SH | >300 | 1670, 1590, 1560 | 13.9, 11.2, 8.6, 8.2, 8.1, 8.0, 3.5, 2.8, 2.3, 1.1 (DMSO-d$_6$) |
| 57 (19) | —SCH₃ | 236 | 1680, 1610, 1550 | 9.1, 9.0, 8.1, 3.5, 2.8, 2.7, 1.3 (CDCl$_3$) |
| 58 (57) | —SCH(CO₂CH₂CH₃)₂ | 164 | 1740, 1680, 1580 | 11.3, 9.0, 8.2, 5.8, 4.3, 3.6, 2.8, 2.3, 1.2, 1.1 (DMSO-d$_6$) |

TABLE 1-3

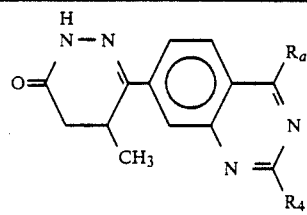

| Compound No. (Example No.) | $R_a$ | $R_4$ | Melting Point (°C.) | IR KBr (cm$^{-1}$) | NMR ($\delta$) ppm (Solvent) |
|---|---|---|---|---|---|
| 59 (61) | —SCH$_3$ | —SCH$_3$ | 245 to 246 | 1700 1610 | 11.2, 7.9, 3.5, 2.7, 2.6, 2.3, 1.1 (DMSO-d$_6$) |
| 60 (62) | —NHCH$_3$ | —SCH$_3$ | 137 to 138 | 1680 1620 1590 | 11.1, 8.4, 8.1, 7.8, 3.5, 3.0, 2.7, 2.5, 2.3, 1.1 (DMSO-d$_6$) |
| 61 (63) | —NH(CH$_2$)$_2$CH$_3$ | —SCH$_3$ | 199 | 1670 1620 1570 | 11.1, 8.4, 8.2, 7.8, 3.5, 2.8, 2.3, 1.7, 1.1 0.9 (DMSO-d$_6$) |
| 62 (64) | —NH(CH$_2$)$_2$CH$_3$ | —NHCH$_3$ | 225 to 231 | 1680 1600 | 11.2, 7.9, 7.7, 7.5, 6.4, 3.4, 2.8, 2.3, 1.6, 1.1, 0.9 (DMSO-d$_6$) |
| 63 (65) | —OCH$_3$ | —CH$_3$ | 232 (decomp.) | 1690 1620 1580 | 11.1, 8.0, 4.1, 2.8, 2.7, 2.3, 1.2 (DMSO-d$_6$) |
| 64 (66) | —NHCH$_3$ | —CH$_3$ | 151 to 153 | 1720 1590 | 11.1, 8.1, 7.8, 3.5, 3.0, 2.8, 2.5, 2.3, 1.1 (DMSO-d$_6$) |
| 65 (67) | —NHCH$_2$—⌬ | —CH$_3$ | 115 (decomp.) | 1680 1570 | 11.0, 8.6, 8.2, 7.9, 7.3, 4.8, 3.5, 2.8, 2.4, 2.3, 1.1 (DMSO-d$_6$) |

TABLE 1-4

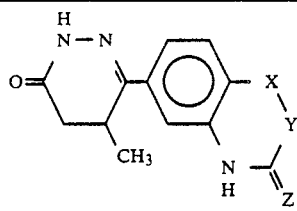

| Compound No. (Example No.) | X—Y | Z | Melting Point (°C.) | IR KBr (cm$^{-1}$) | NMR ($\delta$) ppm (Solvent) |
|---|---|---|---|---|---|
| 66 (68) | NH$_2$<br>\|<br>—C=N— | O | 230 to 236 | 1680 1620 | 11.2, 8.0, 7.8, 7.5, 3.5, 2.8, 2.3, 1.1 (DMSO-d$_6$) |
| 67 (69) | NH CH$_3$<br>\|\| \|<br>—C—N— | O | 271 to 273 | 1680 1620 | 11.1, 8.2, 7.5, 3.4, 2.7, 2.3, 1.1 (DMSO-d$_6$) |
| 68 (70) | N———⌐<br>\|\|     \|<br>—C——N— | O | >300 | 1700 1620 1600 | 11.2, 7.8, 7.5, 3.9, 3.5, 2.7, 2.3, 1.1 (DMSO-d$_6$) |

TABLE 1-4-continued

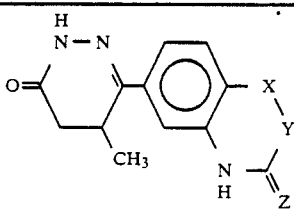

| Compound No. (Example No.) | X—Y | Z | Melting Point (°C.) | IR KBr (cm⁻¹) | NMR (δ) ppm (Solvent) |
|---|---|---|---|---|---|
| 69 (60) | −C(=S)−NH− | S | >300 | 1670 1620 1600 | 11.2, 8.2, 7.7, 3.5, 2.7, 2.3, 1.1 (DMSO-$d_6$) |

TABLE 1-5

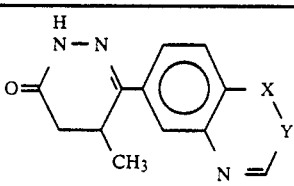

| Compound No. (Example No.) | X—Y | Melting Point (°C.) | IR KBr (cm⁻¹) | NMR (δ) ppm (Solvent) |
|---|---|---|---|---|
| 70 (58) | −C(=C(COOC$_2$H$_5$)$_2$)−NH− | 173 to 175 | 1720 1680 1640 | 12.9, 11.3, 11.2, 9.3, 8.3, 8.2, 7.9, 7.6, 6.2, 4.2, 3.7, 3.5, 2.8, 2.3, 1.2 (DMSO-$d_6$) |
| 71 (71) | −CH$_2$−NH− | 263 (decomp.) | 1680 1600 1570 | 10.9, 7.3, 7.1, 6.9, 4.5, 3.3, 2.7, 2.3, 1.1 (DMSO-$d_6$) |
| 72 (73) | −C(=N−CH$_2$−CH$_2$)−N− (imidazoline) | 280 to 282 | 1680 1620 1600 | 11.1, 8.0, 7.9, 7.8, 4.1, 3.9, 3.5, 2.7, 2.2, 1.1 (DMSO-$d_6$) |
| 73 (74) | −C(=N−CH=CH)−N− (imidazole) | 271 to 273 | 1700 1640 1620 | 11.2, 9.7, 8.7, 8.5, 8.4, 8.3, 3.6, 2.8, 2.3, 1.1 (DMSO-$d_6$) |

TABLE 1-6

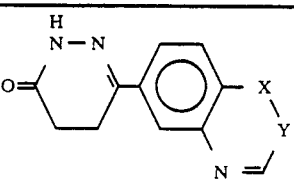

| Compound No. (Example No.) | X—Y | Melting Point (°C.) | IR KBr (cm⁻¹) | NMR (δ) ppm (Solvent) |
|---|---|---|---|---|
| 74 (75) | −C(NHCH$_3$)=N− | 280 to 283 | 1680 1640 1620 | 11.0, 8.2, 8.0, 7.7, 3.4, 3.3, 3.0 (DMSO-$d_6$) |

TABLE 1-6-continued

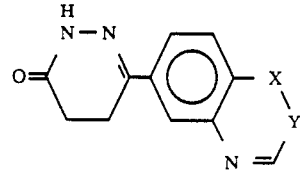

| Compound No. (Example No.) | X—Y | Melting Point (°C.) | IR KBr (cm⁻¹) | NMR (δ) ppm (Solvent) |
|---|---|---|---|---|
| 75 (76) | −C(NHCH$_3$)=N− | >300 | 1660 1600 | 11.0, 8.4, 8.2, 7.9, 3.1, 3.0, 2.6 (DMSO-$d_6$) |
| 76 (77) | −C(SH)=N− | >300 | 1640 1610 1560 | 11.1, 8.6, 8.2, 7.7, 3.0, 2.5 (DMSO-$d_6$) |
| 77 (78) | −C(SCH$_3$)=N− | 273 to 277 | 1680 1620 1560 | 11.0, 9.0, 8.1, 3.1, 2.7, 2.6 (DMSO-$d_6$) |
| 78 (79) | −C(NHCH$_2$−C$_6$H$_5$)=N− | 304 (decomp.) | 1700 1620 1580 | 11.0, 8.8, 8.4, 8.3, 7.9, 7.3, 4.8, 3.1, 2.5 (DMSO-$d_6$) |

The cardiotonic activity and the acute toxicity of representative Compound (I) are shown below referring to experimental examples.

EXPERIMENTAL EXAMPLE 1

Cardiotonic Activity of Compound (I)

Adult male and female mongrel dogs ranging in body weight from 8 to 15 kg were anesthetized by intravenous administration of 30 mg/kg of sodium salt of pentobarbital. Under artificial respiration, a catheter-type pressure transducer was retrogressively inserted into the left ventricle through the left carotid artery to measure the blood pressure in the ventricle. The peripheral blood pressure was measured with a pressure transducer which was inserted into the femoral artery through a catheter. The myocardial contractility was determined by measuring the parameter dp/dt$_{max}$ (the maximum value of primary differential of the blood pressure in the left ventricle), and the heart rate was determined by counting the ECG waves (limb lead II) with a tachometer. During the determination, the anesthesia was sustained by means of inhalation of halothane and dinitrogen oxide. At the same time, a muscle relaxant (pancronium bromide) was continuously injected into the left forelimb vein at a rate of 0.1 mg/kg/hour. In this manner, a stable anesthetic state could be maintained for a sufficiently long period of time.

The test compounds were dissolved in PEG-400 and administered through the right forelimb vein (i.v.) at a dose shown in Table 2.

The maximum changes of myocardiac contractility, heart rate and mean peripheral blood pressure during 60 minutes after the administration based on the values before the administration were determined as well as the duration of the change in myocardiac contractility.

The results are shown in Table 2.

TABLE 2

| Compound | Number of Cases | Dose (i.v.) (mg/kg) | Change of dp/dt$_{max}$ (%) | Max. Change of Heart Rate (%) | Max. Change of Blood Pressure (%) | Duration of Action (min.) |
|---|---|---|---|---|---|---|
| 1 | 2 | 0.03 | 12.7 | 2.7 | −2.6 | 15 |
| 2 | 2 | 0.01 | 10.6 | 1.9 | −8.7 | 5 |
| 3 | 2 | 0.01 | 3.3 | 1.8 | −3.3 | — |
| 4 | 2 | 0.01 | 4.6 | 4.6 | −8.2 | — |
| 5 | 3 | 0.03 | 42.3 ± 5.1 | 13.8 ± 3.3 | −31.1 ± 3.3 | >60 |
| 7 | 3 | 0.01 | 9.2 ± 1.9 | 1.7 ± 0.9 | −8.9 ± 3.5 | 5 |
| 8 | 2 | 0.01 | 9.0 | 8.6 | −7.0 | — |
| 9 | 2 | 0.01 | 5.5 | 1.7 | 3.7 | — |
| 10 | 2 | 0.03 | 8.0 | 5.1 | 3.1 | — |
| 11 | 3 | 0.01 | 56.6 ± 19.8 | 10.5 ± 10.0 | −9.3 ± 3.6 | >60 |
| 12 | 3 | 0.03 | 78.3 ± 2.5 | 24.7 ± 6.2 | −16.5 ± 4.2 | >60 |
| 13 | 3 | 0.01 | 38.8 ± 1.4 | 13.2 ± 2.4 | −18.1 ± 5.3 | >60 |
| 14 | 3 | 0.01 | 49.5 ± 1.7 | 15.0 ± 3.8 | −34.5 ± 9.6 | >60 |
| 15 | 3 | 0.01 | 55.7 ± 3.9 | 15.5 ± 4.6 | −35.9 ± 10.4 | >60 |
| 16 | 3 | 0.01 | 40.6 ± 4.3 | 15.6 ± 4.8 | −25.3 ± 0.7 | >60 |
| 17 | 3 | 0.01 | 67.7 ± 10.4 | 9.6 ± 2.8 | −28.3 ± 1.8 | >60 |
| 19 | 3 | 0.01 | 49.8 ± 10.3 | 17.6 ± 10.3 | −24.4 ± 11.4 | >60 |
| 20 | 3 | 0.01 | 46.9 ± 2.3 | 17.2 ± 8.8 | −9.3 ± 4.3 | >60 |
| 21 | 3 | 0.01 | 37.7 ± 12.4 | 21.5 ± 3.2 | −22.8 ± 4.3 | 60 |
| 22 | 2 | 0.01 | 20.2 | 14.3 | −18.0 | 20 |
| 23 | 3 | 0.01 | 22.2 ± 8.2 | 9.3 ± 6.7 | −11.3 ± 2.7 | 30 |
| 24 | 2 | 0.01 | 8.1 | 6.9 | −15.6 | — |
| 25 | 3 | 0.01 | 22.9 ± 5.3 | 2.7 ± 2.1 | −9.7 ± 3.1 | >60 |
| 26 | 2 | 0.01 | 4.6 | 0.7 | −2.8 | — |
| 27 | 2 | 0.01 | 28.6 | 6.2 | −8.1 | >60 |
| 28 | 3 | 0.01 | 41.0 ± 6.3 | 8.8 ± 3.2 | −15.1 ± 8.7 | >60 |
| 29 | 3 | 0.01 | 35.8 ± 11.2 | 21.3 ± 9.2 | −28.3 ± 3.7 | 50 |
| 30 | 3 | 0.01 | 35.5 ± 7.3 | 9.1 ± 2.9 | −15.4 ± 5.9 | >60 |
| 31 | 2 | 0.01 | 21.2 | 7.7 | −19.5 | >60 |
| 32 | 3 | 0.01 | 45.9 ± 8.7 | 13.3 ± 5.6 | −32.0 ± 0.7 | >60 |
| 33 | 3 | 0.01 | 54.5 ± 3.0 | 11.0 ± 5.2 | −26.8 ± 8.0 | >60 |
| 34 | 3 | 0.01 | 59.5 ± 11.0 | 25.0 ± 1.7 | −24.0 ± 8.5 | >60 |
| 35 | 3 | 0.01 | 43.0 ± 7.4 | 12.0 ± 3.8 | −29.8 ± 3.0 | >60 |
| 36 | 3 | 0.01 | 61.5 ± 10.2 | 31.4 ± 12.6 | −33.2 ± 6.2 | >60 |
| 38 | 3 | 0.01 | 44.1 ± 11.0 | 16.9 ± 9.9 | −26.9 ± 0.9 | >60 |
| 39 | 3 | 0.01 | 42.5 ± 6.8 | 24.2 ± 3.9 | −23.1 ± 3.8 | >60 |
| 40 | 3 | 0.01 | 31.5 ± 3.4 | 7.8 ± 3.1 | −20.0 ± 8.2 | 50 |
| 41 | 3 | 0.01 | 43.5 ± 5.4 | 14.5 ± 5.2 | −25.0 ± 6.6 | >60 |
| 42 | 3 | 0.01 | 33.2 ± 5.0 | 8.0 ± 4.6 | −29.4 ± 3.8 | >60 |
| 43 | 3 | 0.01 | 54.1 ± | 24.4 ± | −36.0 ± | >60 |

TABLE 2-continued

| Compound | Number of Cases | Dose (i.v.) (mg/kg) | Change of dp/dt$_{max}$ (%) | Max. Change of Heart Rate (%) | Max. Change of Blood Pressure (%) | Duration of Action (min.) |
|---|---|---|---|---|---|---|
| 44 | 2 | 0.01 | 9.5<br>2.9 | 3.6<br>1.4 | 3.8<br>−3.4 | — |
| 45 | 3 | 0.01 | 26.7 ± 8.7 | 5.8 ± 2.0 | −7.6 ± 3.8 | >60 |
| 46 | 2 | 0.01 | 17.2 | 5.0 | −14.7 | 10 |
| 47 | 2 | 0.01 | 10.4 | 3.7 | −4.3 | 10 |
| 48 | 3 | 0.01 | 30.4 ± 3.2 | 10.1 ± 3.4 | −8.4 ± 4.2 | >60 |
| 49 | 3 | 0.01 | 21.4 ± 7.4 | 3.9 ± 2.3 | −7.9 ± 1.2 | >60 |
| 50 | 3 | 0.01 | 39.1 ± 7.9 | 27.3 ± 9.7 | −36.1 ± 1.8 | >60 |
| 51 | 2 | 0.01 | 16.2 | 6.2 | −6.0 | 40 |
| 52 | 3 | 0.01 | 40.3 ± 9.6 | 17.8 ± 6.6 | −18.6 ± 4.6 | >60 |
| 53 | 2 | 0.01 | 12.9 | 2.7 | −10.9 | 30 |
| 54 | 3 | 0.01 | 64.7 ± 3.1 | 17.9 ± 3.2 | −17.9 ± 5.8 | 30 |
| 55 | 3 | 0.01 | 29.0 ± 3.1 | 5.5 ± 1.8 | −14.8 ± 1.9 | >60 |
| 58 | 3 | 0.01 | 11.0 ± 2.9 | 1.2 ± 1.3 | −11.1 ± 3.2 | 20 |
| 59 | 2 | 0.01 | 4.3 | 2.0 | −5.3 | — |
| 60 | 2 | 0.01 | 9.0 | 0.8 | −10.0 | 10 |
| 61 | 2 | 0.01 | 14.3 | 7.4 | −10.5 | 20 |
| 62 | 2 | 0.01 | 11.4 | 12.0 | 5.1 | 10 |
| 63 | 2 | 0.01 | 17.2 | 3.7 | −11.2 | 10 |
| 64 | 3 | 0.01 | 22.8 ± 5.1 | 9.3 ± 5.1 | −9.0 ± 1.8 | 60 |
| 65 | 2 | 0.01 | 13.7 | 3.1 | −8.9 | 30 |
| 66 | 2 | 0.01 | −3.8 | 3.2 | 2.0 | — |
| 67 | 2 | 0.01 | 4.8 | −0.9 | −4.7 | — |
| 68 | 2 | 0.01 | 3.3 | 2.1 | −1.8 | — |
| 69 | 2 | 0.01 | 2.4 | −3.1 | −2.3 | — |
| 70 | 3 | 0.01 | 28.7 ± 11.5 | 6.5 ± 3.4 | −12.8 ± 1.7 | 40 |
| 71 | 2 | 0.01 | 5.2 | 1.7 | −2.5 | — |
| 72 | 2 | 0.01 | 11.8 | 5.5 | −16.2 | 30 |
| 73 | 2 | 0.03 | 18.8 | 2.1 | −12.4 | 30 |
| 74 | 2 | 0.01 | 1.1 | 0.2 | −3.3 | — |
| 75 | 2 | 0.01 | 10.5 | 3.7 | −3.6 | 20 |
| 76 | 2 | 0.01 | 0.6 | 0.3 | −1.9 | — |
| 77 | 2 | 0.01 | 0.4 | 0.0 | −0.9 | — |
| 78 | 2 | 0.01 | 6.8 | 1.1 | −4.1 | — |
| Reference Compounds | | | | | | |
| Pimobendan | 3 | 0.03 | 8.2 ± 1.6 | 5.6 ± 1.2 | −5.9 ± 1.9 | — |
| LY 195115 | 3 | 0.03 | 70.2 ± 9.3 | 16.0 ± 1.3 | −44.0 ± 1.2 | >60 |
| Milrinone | 3 | 0.03 | 37.1 ± 2.4 | 4.2 ± 0.3 | −5.9 ± 5.9 | 40 |

EXPERIMENTAL EXAMPLE 2

Experimental Example 2 Acute Toxicity of Compound (I)

Three dd strain male mice weighing 20±1 g were used for each group and the test compounds were orally administered to the mice. Seven days after the administration, the mice were checked whether still alive or not in order to determine the minimal lethal dose of the compounds.

The results are shown in Table 3.

TABLE 3

| Compound | Minimal Lethal Dose (mg/kg) |
|---|---|
| 12 | 300 |
| 33 | >300 |
| Milrinone | 200 |
| (Reference compound) | |

Cardiotonics containing Compound (I) or pharmaceutically acceptable acid addition salts thereof can be prepared in any form of conventionally employed formulations, e.g., tablets, capsules, syrups, injections, drops and suppositories, and can be administered either orally or non-orally, e.g., by means of intramuscular injection, intravenous injection, intraarterial injection, drip and insertion of suppositories into rectum. Such formulations for oral or non-oral administration can be prepared by known methods and may contain various excipients, lubricants, binders, disintegrators, suspending agents, osmotic pressure regulators, emulsifying agents, and the like.

Examples of the carriers which can be used in the formulations are water, distilled water for injection, physiological saline solution, glucose, fructose, sucrose, mannitol, lactose, starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid ester, and glycerol fatty acid ester.

The dose varies depending on mode of administration, age, body weight and conditions of a patient, etc. For example, in the case of oral administration, it is usually in the range of 0.05 to 200 mg/60 kg/day. In the case of drip, the compounds can be administered at a rate of 0.01 to 5 μg/kg/min. and at a daily dose within the limit of the above daily dose for oral administration.

The present invention is further illustrated by the following examples and reference examples.

EXAMPLE 1

In 30 ml of 40% methylamine solution in methanol was dissolved 1.5 g of Compound e obtained in Reference Example 5, and the solution was stirred at 50° C. for 30 minutes. The crystals precipitated were collected by filtration and dried to give 0.9 g (63%) of 4,5-dihydro-5-methyl-6-[3-methyl-4(3H)-quinazolimin-7-yl]-3(2H)-pyridazinone (Compound 1).

EXAMPLES 2–10

The desired compounds were obtained in a similar manner as in Example 1, employing the conditions shown in Table 4-1. The crude products obtained were purified, where necessary, by means of the above-mentioned chromatography, recrystallization, etc.

TABLE 4-1

| Example | Starting Compound | Reagent | Temperature & Time | Product | Yield |
|---|---|---|---|---|---|
| 2 | Compound e (1.0 g) | 30% Ethylamine 6 ml | 50° C. 30 min. | Compound 2 | 0.8 g (53%) |
| 3 | Compound e (1.5 g) | n-Propylamine 2 ml | 50° C. 30 min. | Compound 3 | 0.9 g (57%) |
| 4 | Compound e (1.5 g) | Isopropylamine 2 ml | 50° C. 2 hrs. | Compound 4 | 1.1 g (70%) |
| 5 | Compound e (0.5 g) | n-Butylamine 2 ml | 100° C. 30 min. | Compound 5 | 0.21 g (35%) |
| 6 | Compound e (1.0 g) | Cyclopropylamine 3.0 ml | Room temp. 3 hrs. | Compound 6 | 0.67 g (65%) |
| 7 | Compound e (0.60 g) | Benzylamine 0.60 ml | Room temp. 5 hrs. | Compound 7 | 0.36 g (50%) |
| 8 | Compound e (0.80 g) | Aniline 0.5 ml | 50° C. 3 hrs. | Compound 8 | 0.71 g (77%) |
| 9 | Compound e (0.30 g) | p-Anisidine 0.30 g | Room temp. 1 hr. | Compound 9 | 0.16 g (40%) |
| 10 | Compound e (1.5 g) | Hydrazine.H$_2$O 3.0 ml | 50° C. 30 min. | Compound 10 | 1.0 g (70%) |

[Note]: Methanol was used as the reaction solvent in the above examples.

EXAMPLE 11

6-(4-aminoquinazolin-7-yl)-4,5-dihydro-5-methyl-3(2H)-pyridazinone (Compound 11) was obtained in a similar manner as in Example 1, except that a mixture of 20 ml of concentrated aqueous ammonia and 20 ml of methanol was used in place of the 40% methylamine solution in methanol. Yield: 0.8 g (59%).

EXAMPLE 12

Compound 11 (0.34 g) obtained in Example 11 was dissolved with heating in 10 ml of 1N hydrochloric acid. The solution was cooled, and the crystals precipitated were collected by filtration and dried to give 0.21 g (54%) of 6-(4-aminoquinazolin-7-yl)-4,5-dihydro-5-methyl3(2H)-pyridazinone monohydrochloride monohydrate (Compound 11').

EXAMPLE 13

Compound 1 (0.29 g) obtained in Example 1 was added to 10 ml of 2N sodium hydroxide and the mixture was stirred at 100° C. for 5 hours. The reaction mixture was neutralized with 1N hydrochloric acid, and the crystals precipitated were collected by filtration and dried to give 0.22 g (76%) of 4,5-dihydro-5-methyl-6-(4-methylamino-quinazolin-7-yl)- 3(2H)-pyridazinone (Compound 12).

EXAMPLES 14–17

The desired compounds were obtained in a similar manner as in Example 13, employing the conditions shown in Table 4-2. The crude products obtained were purified, where necessary, by means of the above-mentioned chromatography, recrystallization, etc.

TABLE 4-2

| Example | Starting Compound | Reagent | Temperature & Time | Product | Yield |
|---|---|---|---|---|---|
| 14 | Compound 2 (0.25 g) | 2N-NaOH 5 ml | 110° C. 2 hrs. | Compound 14 | 0.15 g (60%) |
| 15 | Compound 3 (0.33 g) | 2N-NaOH 5 ml | 90° C. 5 hrs. | Compound 15 | 0.21 g (64%) |
| 16 | Compound 4 (0.33 g) | 2N-NaOH 5 ml | 90° C. 4 hrs. | Compound 16 | 0.15 g (71%) |
| 17 | Compound 6 | 2N-NaOH | 60° C. | Compound 28 | 0.14 g |

TABLE 4-2-continued

| Example | Starting Compound | Reagent | Temperature & Time | Product | Yield |
|---|---|---|---|---|---|
| | (0.67 g) | 20 ml | 30 min. | | (21%) |

[Note]: Dimethylformamide was used as the reaction solvent in the above examples.

EXAMPLE 18

Compound e (0.63 g) obtained in Reference Example 5 was dissolved in a mixture of 10 ml of pyridine and 1 ml of triethylamine, and hydrogen sulfide gas was introduced into the solution at room temperature. After 30 minutes, the crystals precipitated were collected by filtration, washed with water and dried to give 0.51 g (85%) of 4,5-dihydro-6-(4-mercaptoquinazolin-7-yl)-5-methyl-3(2H)-pyridazinone (Compound 56).

EXAMPLE 19

To 0.36 g of Compound 56 obtained in Example 18 were added 10 ml of dimethylformamide, 0.2 ml of triethylamine and 0.1 ml of methyl iodide. The resulting mixture was stirred at room temperature for 30 minutes and then concentrated. Thereafter, water was added to the residue, and the crystals precipitated were collected by filtration and dried to give 0.3 g (79%) of 4,5-dihydro-5-methyl-6-(4-methylthioquinazolin-7-yl)-3(2H)-pyridazinone (Compound 57).

EXAMPLE 20

Compound 57 (0.6 g) obtained in Example 19 was dissolved in a mixture of 10 ml of dimethylformamide, 1 ml of triethylamine and 5ml of aqueous 50% dimethylamine solution. The resulting solution was stirred at 60° C. for 4 hours and then concentrated. Thereafter, water was added to the residue, and the crystals precipitated were collected by filtration and dried to give 0.3 g (51%) of 4,5-dihydro-5-methyl-6-(4-dimethylaminoquinazolin-7-yl)-3(2H)-pyridazinone (Compound 13).

EXAMPLES 21–55

The desired compounds were obtained in a similar manner as in Example 20, employing the conditions shown in Table 4-3. The crude products obtained were purified, where necessary, by means of the above-mentioned chromatography, recrystallization, etc.

TABLE 4-3

| Example | Starting Compound | Reagent | Temperature & Time | Product | Yield |
|---|---|---|---|---|---|
| 21 | Compound 57 (0.60 g) | n-Butylamine 3 ml | Under reflux* 5 hrs. | Compound 17 | 0.14 g (21%) |
| 22 | Compound 57 (0.40 g) | Isobutylamine 5 ml | 100° C. 6 hrs. | Compound 18 | 0.23 g (53%) |
| 23 | Compound 57 (0.40 g) | sec-Butylamine 10 ml | 100° C. 15 hrs. | Compound 19 | 0.12 g (28%) |
| 24 | Compound 57 (0.40 g) | n-Amylamine 5 ml | 100° C. 2 hrs. | Compound 20 | 0.26 g (57%) |
| 25 | Compound 57 (0.40 g) | Isoamylamine 5 ml | 100° C. 6 hrs. | Compound 21 | 0.21 g (46%) |
| 26 | Compound 57 (0.40 g) | n-Hexylamine 2 ml | 100° C. 7 hrs. | Compound 22 | 0.22 g (46%) |
| 27 | Compound 57 (0.40 g) | n-Heptylamine 2 ml | 100° C. 7 hrs. | Compound 23 | 0.33 g (67%) |
| 28 | Compound 57 (0.29 g) | n-Octylamine 1.0 ml | 170° C. 3 hrs. | Compound 24 | 0.26 g (71%) |
| 29 | Compound 57 (0.29 g) | Ethanolamine 1.0 ml | 170° C. 3 hrs. | Compound 25 | 0.13 g (43%) |
| 30 | Compound 57 (0.29 g) | N,N-Dimethylethylenediamine 1.0 ml | 170° C. 2 hrs. | Compound 26 | 0.24 g (74%) |
| 31 | Compound 57 (0.40 g) | 4-(3-Aminopropyl)-morpholine 0.3 ml | 170° C. 4 hrs. | Compound 27 | 0.37 g (69%) |
| 32 | Compound 57 (0.40 g) | Cyclopentylamine 5 ml | 100° C. 6 hrs. | Compound 29 | 0.37 g (82%) |
| 33 | Compound 57 (0.29 g) | Cyclohexylamine 2.0 ml | 170° C. 6 hrs. | Compound 30 | 0.22 g (65%) |
| 34 | Compound 57 (0.40 g) | Cyclooctylamine 0.7 ml | 150° C. 5 hrs. | Compound 31 | 0.16 g (31%) |
| 35 | Compound 57 (0.29 g) | Allylamine 1.0 ml | 170° C. 6 hrs. | Compound 32 | 0.08 g (27%) |
| 36 | Compound 57 (0.29 g) | Benzylamine 0.33 ml | 170° C. 4 hrs. | Compound 33 | 0.16 g (46%) |
| 37 | Compound 57 (0.40 g) | o-Methylbenzylamine 5 ml | 150° C. 6 hrs. | Compound 34 | 0.06 g (12%) |
| 38 | Compound 57 (0.40 g) | p-Methylbenzylamine 5 ml | 130° C. 8 hrs. | Compound 35 | 0.20 g (40%) |
| 39 | Compound 57 (0.40 g) | o-Methoxybenzylamine 5 ml | 130° C. 4 hrs. | Compound 36 | 0.14 g (27%) |
| 40 | Compound 57 | m-Methoxybenzyl- | 130° C. | Compound 37 | 0.16 g |

TABLE 4-3-continued

| Example | Starting Compound | Reagent | Temperature & Time | Product | Yield |
|---|---|---|---|---|---|
| | (0.40 g) | amine 5 ml | 4 hrs. | | (30%) |
| 41 | Compound 57 (0.40 g) | p-Methoxybenzyl-amine 2 ml | 130° C. 6 hrs. | Compound 38 | 0.24 g (46%) |
| 42 | Compound 57 (0.40 g) | p-Fluorobenzyl-amine 3 ml | 150° C. 2 hrs. | Compound 39 | 0.15 g (29%) |
| 43 | Compound 57 (0.40 g) | o-Chlorobenzyl-amine 3 ml | 150° C. 8 hrs. | Compound 40 | 0.19 g (36%) |
| 44 | Compound 57 (0.40 g) | m-Chlorobenzyl-amine 3 ml | 150° C. 8 hrs. | Compound 41 | 0.36 g (68%) |
| 45 | Compound 57 (0.40 g) | p-Chlorobenzyl-amine 3 ml | 150° C. 8 hrs. | Compound 42 | 0.18 g (34%) |
| 46 | Compound 57 (0.40 g) | β-Phenylethylamine 5 ml | 130° C. 7 hrs. | Compound 43 | 0.24 g (48%) |
| 47 | Compound 57 (0.40 g) | Homoveratrylamine 5 ml | 130° C. 5 hrs. | Compound 44 | 0.27 g (46%) |
| 48 | Compound 57 (0.29 g) | Aniline 1.0 ml | 170° C. 5 hrs. | Compound 45 | 0.23 g (69%) |
| 49 | Compound 57 (0.40 g) | m-Chloroaniline 3 ml | 150° C. 2 hrs. | Compound 46 | 0.19 g (37%) |
| 50 | Compound 57 (0.40 g) | p-Chloroaniline 3 g | 150° C. 2 hrs. | Compound 47 | 0.09 g (18%) |
| 51 | Compound 57 (0.29 g) | 3-Picolylamine 0.12 ml | 170° C. 8 hrs. | Compound 48 | 0.08 g (23%) |
| 52 | Compound 57 (0.40 g) | 4-Picolylamine 5 ml | 100° C. 7 hrs. | Compound 49 | 0.08 g (16%) |
| 53 | Compound 57 (0.40 g) | 2-(2-Aminoethyl)-pyridine 3 ml | 130° C. 4 hrs. | Compound 50 | 0.10 g (20%) |
| 54 | Compound 57 (0.29 g) | Piperazine 0.5 g | 170° C. 5 hrs. | Compound 51 | 0.14 g (35%) |
| 55 | Compound 57 (0.40 g) | Piperidine 8.0 ml | 100° C.* 5 hrs. | Compound 52 | 0.36 g (80%) |

[Note]: The reactions marked with * were carried out without using any solvents, and the other reactions were carried out in dimethylsulfoxide.

EXAMPLE 56

Compound 11 (0.20 g) obtained in Example 11 was dissolved in 5 ml of pyridine, and 0.1 ml of ethyl chloroformate was added to the solution. The resulting mixture was stirred at room temperature for 3 hours and then concentrated. Water was added to the residue, and the crystals precipitated were collected by filtration and dried to give 0.21 g (82%) of 6-(4-ethoxycarbonylamino-quinazolin-7-yl)-4,5-dihydro-5-methyl-3(2H)-pyridazinone (Compound 53).

EXAMPLE 57

Diethyl bromomalonate (2.4 ml) was added to a mixture of 3.7 g of Compound 56 obtained in Example 18, 13.8 ml of triethylamine and 100 ml of dimethylformamide. The resulting mixture was stirred at room temperature for 2 hours and then concentrated. The residue was subjected to partition between water and chloroform, and the organic layer was dried and concentrated. The residue was purified by means of column chromatography using 150 g of silica gel and then crystallized from diethyl ether to give 3.43 g (59%) of diethyl[7-(2,3,4,5-tetrahydro-5-methyl-3-oxo-2H-pyridazin-6-yl)quinazolin-4-ylthio]malonate (Compound 58).

EXAMPLE 58

A mixture of 2.7 g of Compound 58 obtained in Example 57, 1.9 g of triphenylphosphine, 5.7 g of potassium carbonate and 20 ml of dimethylformamide was stirred at 120° C. for 3 hours. After being cooled to room temperature, the mixture was subjected to partition between water and ethyl acetate. The pH of the water layer was adjusted to 4 with 1N hydrochloric acid, and the crystals precipitated were collected by filtration and dried to give 1.4 g (56%) of diethyl[7-(2,3,4,5-tetrahydro-5-methyl-3-oxo-2H-pyridazin-6-yl)quinazolin-4-yl]malonate (Compound 70).

EXAMPLE 59

A mixture of 0.77 g of Compound 70 obtained in Example 58, 20 ml of ethanol and 7.0 ml of 2N sodium hydroxide was stirred at 90° C. for 2 hours. Then the mixture was concentrated, neutralized with 1N hydrochloric acid and subjected to partition between water and chloroform. The organic layer was dried and concentrated, and the residue was crystallized from methanol to give 0.34 g (70%) of 4,5-dihydro-5-methyl-6-(4-methylquinazolin-7-yl)-3(2H)-pyridazinone (Compound 55).

EXAMPLE 60

A mixture of 4.5 g of Compound d obtained in Reference Example 4, 40 ml of pyridine and 5 ml of carbon disulfide was stirred at 100° C. for 4 hours. Thereafter, water was added to the mixture, and the crystals precipitated were collected by filtration and dried to give 5.5 g (89%) of 4,5-dihydro-5-methyl-6-(2,4-dimercaptoquinazolin-7-yl)-3(2H)-pyridazinone (Compound 69).

EXAMPLE 61

Compound 69 (0.9 g) obtained in Example 60 was dissolved in a mixture of 30 ml of methanol and 2 ml of 2N sodium hydroxide, and then 0.40 ml of methyl iodide was added to the solution. After the mixture was stirred at room temperature for 1 hour, water was added thereto, and the crystals precipitated were collected by filtration and dried to give 0.87 g (89%) of 4,5-dihydro-5-methyl-6-[2,4-bis(methylthio)quinazolin-7-yl]-3(2H)-pyridazinone (Compound 59).

EXAMPLE 62

In 50 ml of 40% methylamine solution in methanol was suspended 0.40 g of Compound 59 obtained in Example 61. The suspension was stirred at 60° C. for 3 hours and then concentrated. Thereafter, water was added to the residue, and the crystals precipitated were collected by filtration and dried to give 0.34 g (89%) of 4,5-dihydro-5-methyl-6-(4-methylamino-2-methylthioquinazolin-7-yl)-3(2H)-pyridazinone (Compound 60).

EXAMPLE 63

The same procedure as in Example 62 was repeated, except that 40% n-propylamine solution in methanol was used in place of 40% methylamine solution in methanol. As a result, 0.12 g (39%) of 4,5-dihydro-5-methyl-6-(2-methyl-thio-4-n-propylaminoquinazolin-7-yl)-3(2H)-pyridazinone (Compound 61) was obtained.

EXAMPLE 64

Compound 61 (0.40 g) obtained in Example 63 was dissolved in 20 ml of 50% acetic acid, and then 0.50 g of potassium permanganate was added to the solution at 5° to 10° C., followed by stirring for 10 minutes. After 100 ml of water was added, the mixture was extracted 5 times with 20 ml of chloroform. The combined chloroform layer was added to 40% methylamine solution in methanol and the mixture was stirred at 60° C. for 10 hours. The resulting mixture was concentrated and subjected to partition between water and chloroform. The organic layer was dried and then concentrated. The residue was crystallized from a mixture of dimethylformamide and water to give 0.27 g (69%) of 4,5-dihydro-5-methyl-6-(2-methylamino-4-n-propylaminoquinazolin-7-yl)-3(2H)-pyridazinone (Compound 62).

EXAMPLE 65

In 30 ml of pyridine was dissolved 3.0 g of Compound d obtained in reference Example 4, and 3 ml of acetylchloride was added to the solution. The mixture was stirred at 80° C. for 3 hours and then concentrated. The residue was subjected to partition between water and chloroform, and the organic layer was concentrated. To the residue were added 50 ml of methanol, 50 ml of water and 2.0 g of potassium carbonate, followed by stirring at 80° C. for 3 hours. The resulting mixture was concentrated, and the crystals precipitated were collected by filtration and dried to give 1.1 g (28%) of 4,5-dihydro-6-(4-methoxy-2-methylquinazolin-7-yl)-5-methyl-3(2H)-pyridazinone (Compound 63).

EXAMPLE 66

In 20 ml of 40% methylamine solution in methanol was suspended 0.50 g of Compound 63 obtained in Example 65. The suspension was heated under reflux with stirring for 4 hours and then concentrated. The residue was subjected to partition between water and chloroform, and the organic layer was dried and concentrated. The residue was crystallized from a mixture of dimethylformamide and water to give 0.38 g (76%) of 4,5-dihydro-5-methyl-6-(4-methylamino2-methylquinazolin-7-yl)-3(2H)-pyridazinone (Compound 64).

EXAMPLE 67

A mixture of 0.76 g of Compound 64 obtained in Example 66, 15 ml of benzylamine and 15 ml of dimethylsulfoxide was stirred at 150° C. for 3 hours, and then concentrated. The residue was subjected to partition between water and chloroform, and the organic layer was dried and concentrated. The residue was purified by column chromatography using 100 g of silica gel to give 0.31 g (32%) of 6-(4-benzylamino-2-methylquinazolin-7-yl)-4,5-dihydro-5-methyl-3(2H)-pyridazinone (Compound 65).

EXAMPLE 68

In 5 ml of dimethylsulfoxide was dissolved 0.30 g of Compound f obtained in Reference Example 6. The solution was heated at 150° C. and stirred for 2 hours with introduction of ammonia gas. Water was added to the reaction mixture, and the crystals precipitated were collected by filtration and dried to give 0.2 g (74%) of 6-(4-amino-1,2-dihydro-2-oxo-1H-quinazolin-7-yl)-4,5-dihydro-5-methyl-3(H)-pyridazinone (Compound 66).

EXAMPLE 69

The same procedure as in Example 68 was repeated, except that 1 ml of 40% methylamine solution in methanol was added dropwise instead of the introduction of ammonia gas. As a result, 0.21 g (74%) of 4,5-dihydro-6-(1,2,3,4-tetrahydro-4-imino-3-methyl-2-oxo-1H,3H-quinazolin-7-yl)-5-methyl-3(2H)-pyridazinone (Compound 67) was obtained.

EXAMPLE 70

The same procedure as in Example 68 was repeated, except that 1 ml of ethylenediamine was added instead of the introduction of ammonia gas. As a result, 0.20 g (67%) of 4,5-dihydro-6-(2,3-dihydro-5-oxo-6H-imidazo[1,2-c]-quinazolin-8-yl)-5-methyl-3(2H)-pyridazinone (Compound 68) was obtained.

EXAMPLE 71

In 10 ml of dimethylformamide was dissolved 1.0 g of Compound 57 obtained in Example 19, and 5.0 g of Raney nickel was added to the solution, followed by stirring at 60° C. for 1 hour. The catalyst was filtered off, and the filtrate was concentrated. Water was added to the residue, and the crystals precipitated were collected by filtration and dried to give 0.22 g (26%) of 4,5-dihydro-6-(3,4-dihydroquinazolin-7-yl)-5-methyl-3(2H)-pyridazinone (Compound 71).

EXAMPLE 72

In 20 ml of chloroform was dissolved 0.25 g of Compound 71 obtained in Example 71, and 2.0 g of manganese dioxide was added to the solution, followed by stirring at room temperature for 1 hour. Insoluble substances were filtered off, and the filtrate was concentrated. The residue was crystallized by the addition of diethyl ether to give 0.2 g (83%) of 4,5-dihydro-5-methyl-6-(7-quinazolinyl)-3(2H)-pyridazinone (Compound 54).

EXAMPLE 73

The same procedure as in Example 6 was repeated, except that 3 ml of ethylenediamine was used instead of cyclopropylamine. As a result, 0.6 g (61%) of 4,5-dihydro(2,3-dihydroimidazo[1,2-c]quinazolin-8-yl)-5-methyl-3(2H)-pyridazinone (Compound 72) was obtained.

EXAMPLE 74

A mixture of 0.35 g of Compound 10 obtained in Example 10 and 10 ml of ethyl orthoformate was stirred at 150° C. for 3 hours. The mixture was then concentrated and water was added to the residue. The crystals precipitated were collected by filtration and dried to give 0.28 g (77%) of 4,5-dihydro-5-methyl-6-(s-triazolo[1,5-c]quinazolin-9-yl)-3(2H)-pyridazinone (Compound 73).

EXAMPLE 75

In 10 ml of 40% methylamine solution in methanol was dissolved 0.30 g of Compound k obtained in Reference Example 11. The resulting solution was stirred at room temperature for 1 hour, and the crystals precipitated were collected by filtration and dried to give 0.23 g (82%) of 4,5-dihydro-6-[3-methyl-4(3H)-quinazolinimin-7-yl]-3(2H)-pyridazinone (Compound 74).

EXAMPLE 76

A mixture of 0.16 g of Compound 74 obtained in Example 75, 10 ml of 40% methylamine solution in methanol and 10 ml of dimethylformamide was stirred under reflux for 3 hours. After cooling, the crystals precipitated were collected by filtration and dried to give 0.08 g (44%) of 4,5-dihydro-6-(4-methylaminoquinazolin-7-yl)-3(2H)-pyridazinone (Compound 75).

EXAMPLE 77

The same procedure as in Example 18 was repeated, except that 0.67 g of Compound k obtained in Reference Example 11 was used instead of Compound e. As a result, 0.49 g (77%) of 4,5-dihydro-6-(4-mercaptoquinazolin-7-yl)-3(2H)-pyridazinone (Compound 76) was obtained.

EXAMPLE 78

The same procedure as in Example 19 was repeated, except that 0.10 g of Compound 76 obtained in Example 77 was used instead of Compound 56. As a result, 0.10 g (95%) of 4,5-dihydro-6-(4-methylthioquinazolin-7-yl)-3(2H)-pyridazinone (Compound 77) was obtained.

EXAMPLE 79

The same procedure as in Example 36 was repeated, except that 0.29 g of Compound 77 prepared in Example 78 was used instead of Compound 57. As a result, 0.06 g (17%) of 6-(4-benzylaminoquinazolin-7-yl)-4,5-dihydro-3(2H)-pyridazinone (Compound 78) was obtained.

REFERENCE EXAMPLE 1

To 300 ml of fuming nitric acid was added by small portions 51 g of 3-(4-bromobenzoyl)butyric acid with stirring over 2 hours, during which the internal temperature of the reaction mixture was maintained at 10° to 20° C. The resulting mixture was poured into 1 liter of ice water and then extracted with chloroform. The chloroform layer was washed with water and concentrated. The residue was crystallized from water to give 46 g (77%) of 3-(4-bromo-3-nitrobenzoyl)butyric acid [Compound a; Compound (IV) wherein $R_3=CH_3$].

mp : 111°–113° C.
IR (KBr) $cm^{-1}$: 1700, 1690, 1600.
NMR ($CDCl_3$) ppm: 8.3, 7.9, 3.8, 3.0, 2.5, 1.2.

REFERENCE EXAMPLE 2

To a mixture of 300 ml of acetic acid and 52 ml of hydrazine monohydrate was added 52 g of Compound a obtained in Reference Example 1. The resulting mixture was stirred at 100° C. for 3 hours and then concentrated to about one-third of its original volume. 500 ml of water was added to the concentrate, and the crystals precipitated were collected by filtration and dried to give 54 g (100%) of 6-(4-bromo-3-nitrophenyl)-4,5-dihydro-5-methyl-3(2H)-pyridazinone [Compound b; Compound (V) wherein $R_3=CH_3$].

mp : 196° C.
IR (KBr) $cm^{-1}$: 1720, 1620, 1540.
NMR ($CDCl_3$) ppm: 11.2, 8.3, 8.0, 3.4, 2.8, 2.3, 1.1.

REFERENCE EXAMPLE 3

In 100 ml of dimethylformamide was dissolved 19 g of Compound b obtained in Reference Example 2, and 6.7 g of cuprous cyanide was added to the solution, followed by stirring at 110° C. for 2 hours. After being cooled, the mixture was poured into a mixture of 30 ml of ethylene-diamine and 200 ml of water. Insoluble substances were filtered off, and the filtrate was subjected to partition between water and chloroform. The chloroform layer was dried and then concentrated. The residue was crystallized from a mixture of chloroform and diethyl ether to give 6.9 g (44%) of 6-(4-cyano-3-nitrophenyl)-4,5-dihydro-5-methyl-3(2H)-pyridazinone [Compound c; Compound (VI) wherein $R_3=CH_3$]

mp : 208°–209° C.
IR (KBr) $cm^{-1}$: 2210, 1680, 1600.
NMR ($CDCl_3$) ppm: 11.4, 8.7, 8.3, 3.5, 2.8, 2.3, 1.1.

REFERENCE EXAMPLE 4

A mixture of 4 ml of concentrated hydrochloric acid and 1.4 g of stannous chloride dihydrate was ice-cooled, and 0.52 g of Compound c obtained in Reference Example 3 was added thereto. The resulting mixture was stirred for 10 minutes and adjusted to pH 10 by the addition of 5N sodium hydroxide. The crystals precipitated were collected by filtration and then dissolved in dimethylformamide. Insoluble substances were filtered off, and the filtrate was concentrated. The residue was crystallized by the addition of water to give 0.4 g (87%) of 6-(3-amino-4-cyanophenyl)-4,5-dihydro-5-methyl-3(2H)-pyridazinone [Compound d; Compound (IIa) wherein $R_3=CH_3$]

mp : 208°–209° C.
IR (KBr) $cm^{-1}$: 2200, 1680, 1640.
NMR (DMSO-$d_6$) ppm: 11.0, 7.4, 7.2, 7.0, 6.1, 3.2, 2.7, 2.3, 1.1.

REFERENCE EXAMPLE 5

To 1 g of Compound d obtained in Reference Example 4 were added 10 ml of ethyl orthoformate and 1 ml of dimethylformamide. The resulting mixture was stirred under reflux for 5 hours and then concentrated. The residue was crystallized from a mixture of ethanol and diethyl ether to give 0.3 g (24%) of 6-(4-cyano-3-ethoxymethyleneamino-phenyl)-4,5-dihydro-5-methyl- 3(2H)-pyridazinone [Compound e; Compound (IIb) wherein $R_3=CH_3$, $R_4=H$ and $R_7=C_2H_5$.

mp : 15°–152° C.

IR (KBr) cm$^{-1}$: 2210, 1680, 1630.

NMR (DMSO-d$_6$) ppm: 11.2, 8.1, 7.8, 7.7, 7.5, 4.3, 3.4, 2.7, 2.3, 1.4, 1.1.

REFERENCE EXAMPLE 6

A mixture of 4.5 g of Compound d obtained in Reference Example 4, 2.3 ml of ethyl chloroformate and 40 ml of pyridine was stirred at room temperature for 30 minutes. Then the mixture was concentrated, and water was added to the residue. The crystals precipitated were collected by filtration and dried to give 3.0 g (50%) of 4-(2,3,4,5-tetrahydro-5-methyl-3-oxo-2-H-pyridazin-6-yl)-N-ethoxycarbonylanthranilonitrile [Compound f; Compound (IIc) wherein $R_3=CH_3$ and $R_7=C_2H_5$].

mp : 198°–200° C.

IR (KBr) cm$^{-1}$: 2200, 1740, 1670.

NMR (DMSO-d$_6$) ppm: 11.1, 9.8, 8.9, 8.8, 8.7, 4.2, 2.8, 2.3, 1.2, 1.1.

REFERENCE EXAMPLE 7

The same procedure as in Reference Example 1 was repeated, except that 10.0 g of 3-(4-bromobenzoyl)propionic acid was used instead of 3-(4-bromobenzoyl)-butyric acid. As a result, 7.1 g (59%) of 3-(4-bromo-3-nitrobenzoyl)-propionic acid [Compound g; Compound (IV) wherein $R_3=H$] was obtained.

mp : 145°–147° C.

IR (KBr) cm$^{-1}$: 1690, 1600.

NMR (DMSO-d$_6$) ppm: 8.5, 8.1, 3.3, 2.6.

REFERENCE EXAMPLE 8

The same procedure as in Reference Example 2 was repeated, except that 13.8 g of Compound g obtained in Reference Example 7 was used instead of Compound a. As a result, 5.3 g (37%) of 6-(4-bromo-3-nitrophenyl)-4,5-dihydro-3(2H)-pyridazinone [Compound h; Compound (V) wherein $R_3=H$] was obtained.

mp : 201°–204° C.

IR (KBr) cm$^-$: 1700, 1620.

NMR (DMSO-d$_6$) ppm: 11.1, 8.3, 7.9, 3.0, 2.5.

REFERENCE EXAMPLE 9

The same procedure as in Reference Example 3 was repeated, except that 5.1 g of Compound h obtained in Reference Example 8 was used instead of Compound b. As a result, 3.4 g (81%) of 6-(4-cyano-3-nitrophenyl)-4,5-dihydro-3(2H)-pyridazinone [Compound i; Compound (VI) wherein $R_3=H$] was obtained.

mp : 235°–241° C.

IR (KBr) cm$^-$: 2210, 1680, 1600.

NMR (DMSO-d$_6$) ppm: 11.1, 8.6, 8.2, 3.1, 2.5.

REFERENCE EXAMPLE 10

The same procedure as in Reference Example 4 was repeated, except that 3.3 g of Compound i obtained in Reference Example 9 was used instead of Compound c. As a result, 1.1 g (38%) of 6-(3-amino-4-cyanophenyl)-4,5-di-hydro-3(2H)-pyridazinone [Compound j; Compound (IIa) wherein $R_3=H$] was obtained.

mp : 254°–257° C.

IR (KBr) cm$^{-1}$: 2210, 1680, 1640.

NMR (DMSO-d$_6$) ppm: 11.1, 7.4, 7.1, 6.9, 6.1, 2.9, 2.4.

REFERENCE EXAMPLE 11

The same procedure as in Reference Example 5 was repeated, except that 1.1 g of Compound j obtained in Reference Example 10 was used instead of Compound d. As a result, 1.0 g (72%) of 6-(4-cyano-3-ethoxymethyleneamino-phenyl)-4,5-dihydro-3(2H)-pyridazinone [Compound k; Compound (IIb) wherein $R_3=H$, $R_4=H$ and $R_7=C_2H_5$] was obtained.

mp : 172° C.

IR (KBr) cm$^{-1}$: 2210, 1680, 1640.

NMR (DMSO-d$_6$) ppm: 11.0, 8.1, 7.8, 7.6, 7.5, 4.3, 3.0, 2.5, 1.3.

REFERENCE EXAMPLE 12

The ingredients shown below are uniformly mixed to obtain a powdered or granulated preparation.

| | |
|---|---|
| Compound 12 | 10 parts by weight |
| Heavy magnesium oxide | 10 parts by weight |
| Lactose | 80 parts by weight |

What is claimed is:

1. A compound of the formula:

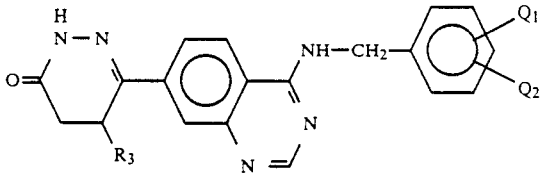

wherein $R_3$ is hydrogen or $C_{1-6}$ alkyl; and $Q_1$ and $Q_2$ are independently hydrogen, $C_{1-4}$ alkyl, hydroxyl, $C_{1-4}$ alkoxyl, amino, mono- or di-$C_{1-4}$ alkyl-substituted amino, nitro or halogen; or a pharmaceutically acceptable acid addition salt thereof.

2. A compound according to claim 1, wherein $R_3$ is methyl and one of $Q_1$ and $Q_2$ is hydrogen and the other is selected from the group consisting of hydrogen, 2-methyl, 4-methyl, 2-methoxy, 4-methoxy, 4-fluoro, 3-chloro and 4-chloro.

3. A pharmaceutical composition comprising a pharmaceutical carrier and, as an active ingredient, an effective cardiotonic amount of a pyridazinone compound as defined by claim 1 or a pharmaceutically acceptable acid addition salt thereof.

* * * * *

UNITED STATES PATENT AND TRADEMARK OFFICE
CERTIFICATE OF CORRECTION

PATENT NO. : 5,063,227
DATED : November 5, 1991
INVENTOR(S) : YUJI NOMOTO, ET AL.

Page 1 of 2

It is certified that error appears in the above-indentified patent and that said Letters Patent is hereby corrected as shown below:

TITLE PAGE

IN [56] REFERENCES CITED

Under U.S. PATENT DOCUMENTS, "Bandorco" should read
   --Bandurco-- and "4,957,920 8/1990" should read
   --4,957,920 9/1990--.

Under U.S. PATENT DOCUMENTS, insert:
   --4,297,360 10/1981 Lesher et al.
    4,361,563 11/1982 Austel et al.
    4,725,686  2/1988 Kuhla et al.--.

Under FOREIGN PATENT DOCUMENTS, insert:
   --0075436 3/1983 EPO
    0161918 11/1985 EPO--.

IN [57] ABSTRACT

"NHCH$_2$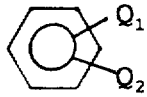" should read --NH—CH$_2$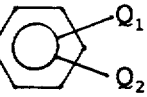--.

COLUMN 9

Lines 5-8, "" should read ----.

UNITED STATES PATENT AND TRADEMARK OFFICE
CERTIFICATE OF CORRECTION

PATENT NO. : 5,063,227
DATED : November 5, 1991
INVENTOR(S) : YUJI NOMOTO, ET AL.

It is certified that error appears in the above-indentified patent and that said Letters Patent is hereby corrected as shown below:

COLUMN 13

Lines 5-8, " 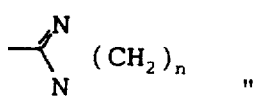 should read -- 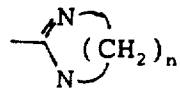 --.

COLUMN 31

Line 53, "Experimental Example 2" should be deleted.

COLUMN 43

Line 3, "15°" should read --150°--.
Line 48, "cm⁻:" should read --$cm^{-1}$:--.
Line 60, "cm⁻:" should read --$cm^{-1}$:--.

Signed and Sealed this

Fourth Day of January, 1994

Attest:

BRUCE LEHMAN

*Attesting Officer*  *Commissioner of Patents and Trademarks*